(12) United States Patent
Kantor et al.

(10) Patent No.: US 11,432,965 B2
(45) Date of Patent: Sep. 6, 2022

(54) MEDICAL BANDAGE FOR THE HEAD, A LIMB OR A STUMP

(71) Applicants: Deborah Kantor, Ponte Verda Beach, FL (US); Sherrin Whiteman, Jacksonville Beach, FL (US)

(72) Inventors: Deborah Kantor, Ponte Verda Beach, FL (US); Sherrin Whiteman, Jacksonville Beach, FL (US)

(*) Notice: Subject to any disclaimer, the term of this patent is extended or adjusted under 35 U.S.C. 154(b) by 436 days.

(21) Appl. No.: 16/153,384

(22) Filed: Oct. 5, 2018

(65) Prior Publication Data
US 2020/0206035 A1    Jul. 2, 2020

(51) Int. Cl.
*A61F 13/00* (2006.01)
*A61F 13/06* (2006.01)
*A61F 13/12* (2006.01)

(52) U.S. Cl.
CPC .. *A61F 13/00038* (2013.01); *A61F 13/00029* (2013.01); *A61F 13/00068* (2013.01); *A61F 13/06* (2013.01); *A61F 13/12* (2013.01); *A61F 2013/00106* (2013.01); *A61F 2013/00119* (2013.01)

(58) Field of Classification Search
CPC .......... A61F 13/00004; A61F 13/00008; A61F 13/00021; A61F 13/00029; A61F 13/00034; A61F 13/00038; A61F 13/00051; A61F 13/00068; A61F 2013/00119; A61F 2013/00123; A61F 2013/0017; A61F 2013/00174; A61F 2013/00187; A61F 2013/00204; A61F 2013/00217; A61F 2013/00604; A61F 2013/00272; A61F 2013/0028; A61F 2013/00289; A61F 13/06; A61F 13/12; A61F 2013/0048; A61F 2013/00574; A61F 2013/00578; A61F 2013/00429; A61F 2013/0094; A61F 2013/00565; A61F 2013/00561; A61F 2013/0057
USPC ............................ 602/58; 604/313, 316, 289
See application file for complete search history.

(56) References Cited

U.S. PATENT DOCUMENTS 3,556,096 A * 1/1971 Fuller ............... A61F 13/00021
    128/888
5,090,410 A * 2/1992 Saper ................. A61B 1/00142
    356/41

(Continued)

*Primary Examiner* — Kim M Lewis
(74) *Attorney, Agent, or Firm* — John Rizvi; John Rizvi, P.A.—The Patent Professor ®

(57) ABSTRACT

A medical bandage is provided, capable of being rapidly, adjustably, intuitively and universally fitted on a head, limb, stump, finger or other body part, such as to conceal and protect a wound. The medical bandage is cap-shaped and deformable, is formed of several layers, and comprises at least one port for obtaining quick access to a wound concealed by the medical bandage. When open, a port can stabilize a drainage tube, or provide a passage through which to easily and rapidly apply a medicine. The medical bandage can be directly fit on the head or other body part, providing an all-in-one dressing, wrap and treatment, and eliminating the need for cumbersome and difficult to manage gauze roll and multiple bandages of various sizes, shapes, and uses. The medical bandage can include one or more sensors for measuring or monitoring body parameters or functions.

29 Claims, 20 Drawing Sheets

(56) References Cited

U.S. PATENT DOCUMENTS

| | | | | |
|---|---|---|---|---|
| 7,296,570 B2* | 11/2007 | Hutchinson | ............... | A61F 7/02 128/201.26 |
| 8,791,315 B2* | 7/2014 | Lattimore | ............... | A61M 1/90 602/46 |
| 2009/0177051 A1* | 7/2009 | Arons | ................... | A61B 5/445 600/306 |
| 2009/0299259 A1* | 12/2009 | Cumming | ............... | A61F 13/12 602/74 |
| 2011/0054283 A1* | 3/2011 | Shuler | ..................... | A61M 1/90 604/319 |
| 2014/0288476 A1* | 9/2014 | Wright | ................... | A61F 13/12 602/48 |
| 2017/0000651 A1* | 1/2017 | Cumming | ......... | A61F 13/00038 |
| 2017/0246041 A1* | 8/2017 | Cumming | ......... | A61F 13/00042 |
| 2018/0263824 A1* | 9/2018 | Ible | ................... | A61F 13/00038 |
| 2019/0021616 A1* | 1/2019 | Day | ................... | A61B 5/02427 |
| 2019/0351092 A1* | 11/2019 | Silver | ................ | A61F 13/0206 |

* cited by examiner

MEDICAL BANDAGE FOR THE HEAD, A LIMB OR A STUMP

FIELD OF THE INVENTION

The present invention relates generally to a medical bandage and, in particular, to a deformable, cap-shaped medical dressing or bandage conveniently shaped to cover a wound on a patient's head, limb, stump, finger or other body part for emergency, post-surgical, or chronic wound care, for instance in the event of a bleeding cranial wound or in the event or curing an amputated limb. The present invention provides access ports to the wound in order to support or stabilize wound drains, or apply medicine to the wound.

BACKGROUND OF THE INVENTION

Typically, a medical bandage or dressing is a covering or wrap that protectively conceals a wounded area of the body in order to stem the flow of body fluids from the wound, absorb body fluids from the wound, ease pain, debride the wound, protect the wound from infection, promote healing of the wound, and/or reduce psychological stress. Medical bandages are used for many different healthcare situations such as for emergency, post-surgical, or chronic care of a wound. Normally, bandages or dressings are in direct contact with the wound, and are covered with an adhesive film to hold them in place. Dressings can be marketed in various configurations; in a first example, dressings are sold alone in rolls, sheets or pads, to be directly applied on or around a body portion; in another example, a dressing and a corresponding adhesive band are sold as an integral product. Generally, dressings are sold in a flat configuration, to cover a substantially flat surface of the body. In the event that a curved surface is to be covered, the dressing is deformed to adopt the shape of the surface. Similarly, in the event that a full perimetric surface must be covered, such as a wrist or knee, the dressing is deformed to wrap around the perimetric surface.

It is well known that traumatic amputations are generally gruesome, devastating injuries that may result in death. Similarly, head injuries often result in trauma to the scalp, skull, or brain. These injuries frequently result in extreme blood loss which can contribute greatly to the associated fatality rate. The time required to control the bleeding of an amputation is vital in reducing blood loss. Often, quickly covering the wounds on the amputated limb or head helps to stop further blood loss during emergency care, and maintaining a suitable bandage can help protect the wound, promote wound healing and prevent infection. However, the dressing and bandage materials known in the art are often cumbersome to handle and difficult to appropriately deform and apply, particularly on an immobilized victim. Due to different settings, injuries, and access to care, medical professionals must use a multitude of sizes, shapes, styles of bandages for covering and treating wounds of the head or limb. In consequence, it is not rare that medical professionals are required to heavily manipulate dressings in order to fit them onto the head or onto a stump, leading to a great loss of time and to an increased risk of the dressings being contaminated or placed ineffectively from such manipulation. A person skilled in the art will clearly understand that the more ready, intuitive, and universally applied the medical devices and instruments are, the more effective and successful the treatment can be for immediate medical and post-traumatic wound care. In addition, promoting wound healing of the head or a limb can be a lengthy process requiring days to months of dressing changes and wound care. Having to repeatedly and manually wind and unwind conventional dressings (not particularly indicated for the head or limb) over the head or limb is cumbersome and extremely labor consuming.

In an attempt to reduce the amount of time needed to obtain a covering that is specifically shaped for the patient's head, some head-specific bandage solutions have been developed. For instance, U.S. Pat. No. 5,031,609 describes a postoperative compression bandage for the head which is formed of two identical flat portions affixed to one another forming a flat body, wherein the body can be wrapped around the patient's head and be secured in place by hook-and-loop fasteners comprised on certain edges of the flat portions. U.S. Patent Application No. 2009/0299259A1 describes a head trauma cap bandage and method which, when applied, applies compression pressure to stop bleeding; the head trauma bandage is cap-shaped and secured to the patient's head by a strap that wraps around the patient's mandible. U.S. Pat. No. 7,887,501 teaches a compressive head dressing comprising an elastomeric layer and a cinch for adjusting to the patient's head.

However, known solutions mainly focus on providing a head-shaped dressing and do not specifically address other problems such as being able to rapidly and efficiently provide treatment of head wounds.

Accordingly, there remains a need in the art to provide an adequate dressing cover for the head, a limb or a stump or an extremity of the human or animal body, which is optimized for such body part, facilitates treatment of wounds and is yet provided at reasonable cost.

SUMMARY OF THE INVENTION

The present invention overcomes the deficiencies of the known art and the problems that remain unsolved by providing a medical bandage specifically designed for the head, a limb, a stump, a finger or other body part, producing a dressing covering that can be rapidly, intuitively, and universally applied in the event of an emergency or trauma. Unlike conventional dressings, the medical bandage disclosed herein can open for rapid easy fitting without further traumatizing a head with patient supine. In addition, the medical bandage disclosed herein is useful for treating ongoing wound care needs, to stabilize and hold drains, view wounds, medicate, and allow for a rapid and universal dressing change which is designed for use for both the head and a limb, as well as other body parts.

The medical bandage presents a three-dimensional cap-like shape having a convex outer surface and a concave inner surface configured to conform to the head, limb, stump, finger or other body part. The medical bandage is formed by several layers of material, namely an internal layer made of a soft, skin compatible fabric, an external layer made of breathable material, and an intermediate absorbent layer or, alternatively or complementarily, an intermediate flexible bladder. Means of adjustment such as side hook-and-loop straps can be included in order to adjust the bandage to the head, limb, stump, finger or other body part and provide necessary compression to coagulate and maintain an intact dressing to cover the wound and promote healing. In some embodiments, the bandage can be partially or totally elastic to provide adjustment. In some embodiments, the medical bandage not only provides a ready-to-apply cover for a wound, but also includes active treating agents such as coagulant agents, antimicrobial agents, heating agents, cooling agents, or a combination thereof. The medical bandage in accordance with the invention may be used not only to cover wounds, but also for other purposes such as treating or preventing hair loss.

In a first implementation of the invention, a medical bandage comprises a deformable main body having an inner surface and an outer surface. The main body is configured to adopt a position in which an inner cavity is delimited by the inner surface for at least partially receiving a head, limb, stump, finger or other body part. At least part of the main body comprises a skin-compatible first layer, a second layer and a non-permeable third layer. The first layer is arranged closer to the inner cavity than the third layer. In turn, the second layer is arranged between the first layer and the third layer and comprises at least one space through which the first and third layers directly face one another. The main body of the bandage further includes at least one through port arranged at the at least one space, for accessing the inner cavity of the main body from outside the main body and through the first, second and third layers, or for stabilizing or supporting a drain or tubing passing through the port.

In a second aspect, the at least one through port can be provided by scored lines and can adopt a closed position in which the scored lines are not torn, and an open position in which the scored lines are torn open providing quick access to the inner cavity.

In another aspect, the second layer can include an absorbent material, and the first layer can be permeable to the passing of fluid from the inner surface towards the second layer.

In another aspect, the main body can further include at least one adjustment strap, configured to adjustably attach two different sections of the main body.

In another aspect, the adjustment strap can be fixedly attached to a first section of the main body and disconnectably attachable to a second section of the main body.

In another aspect, opposite ends of the adjustment strap can be disconnectably attachable to different sections of the main body. For instance and without limitation, the adjustment strap can be disconnectably attachable to the main body by a hook-and-loop connection.

In another aspect, the main body can define a rim delimiting an opening for inserting a head, limb, stump, finger or other body part therethrough towards the inner cavity of the main body. The at least one adjustment strap can be attachable along the rim and parallel to the rim.

In another aspect, the at least one adjustment strap can include two adjustment straps configured to wind with one another and attach to the main body by a respective hook-and-loop connection.

In another aspect, the at least one adjustment strap can include two adjustment straps configured to tie to one another into a knot for compression or securing the bandage.

In another aspect, at least one of the first, second and third layers can include an insulating material such as, but not limited to, biaxially-oriented polyethylene terephthalate (e.g., Mylar®).

In another aspect, the main body can be at least partially elastic to adjustably fit onto a head, limb, stump, finger or other body part.

In another aspect, the first, second and/or third layers can include a plurality of partial portions, which are arranged adjacently to each other forming a cap-shape.

In another aspect, at least two partial portions of the second layer can be separated by a gap, through which the first and third layers directly face one another.

In another aspect, the first layer and third layer can include at least one pair of perforated seams facing the gap.

In another aspect, the plurality of partial portions can include an elongated body portion and two opposite side portions attached to opposite sides of the elongated body portion. One or both of the opposite side portions can be pivotable relative to the elongated body portion and configured to adopt a closed position in which the side portions and elongated body portion form a cap-shaped body.

In another aspect, the main body can include a tearable portion which is configured to be torn off and removed from a remainder of the main body to reduce the height of the main body. The tearable portion, once torn off and removed from said remainder of the main body, is usable as a tourniquet.

In another aspect, the medical bandage can further include at least one sensor for measuring a body condition. The sensor can be carried by the main body and configured to establish wired or wireless communication with an external electronic device for transmitting a measurement to the electronic device.

In another aspect, the at least one sensor can be disconnectably attachable to the at least one through port.

These and other advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

In this document, relational terms such as "first" and "second", "top" and "bottom," and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a . . . " does not, without more constraints, preclude the existence of additional identical elements in the process, method, article, or apparatus that comprises the element.

Figure 1:
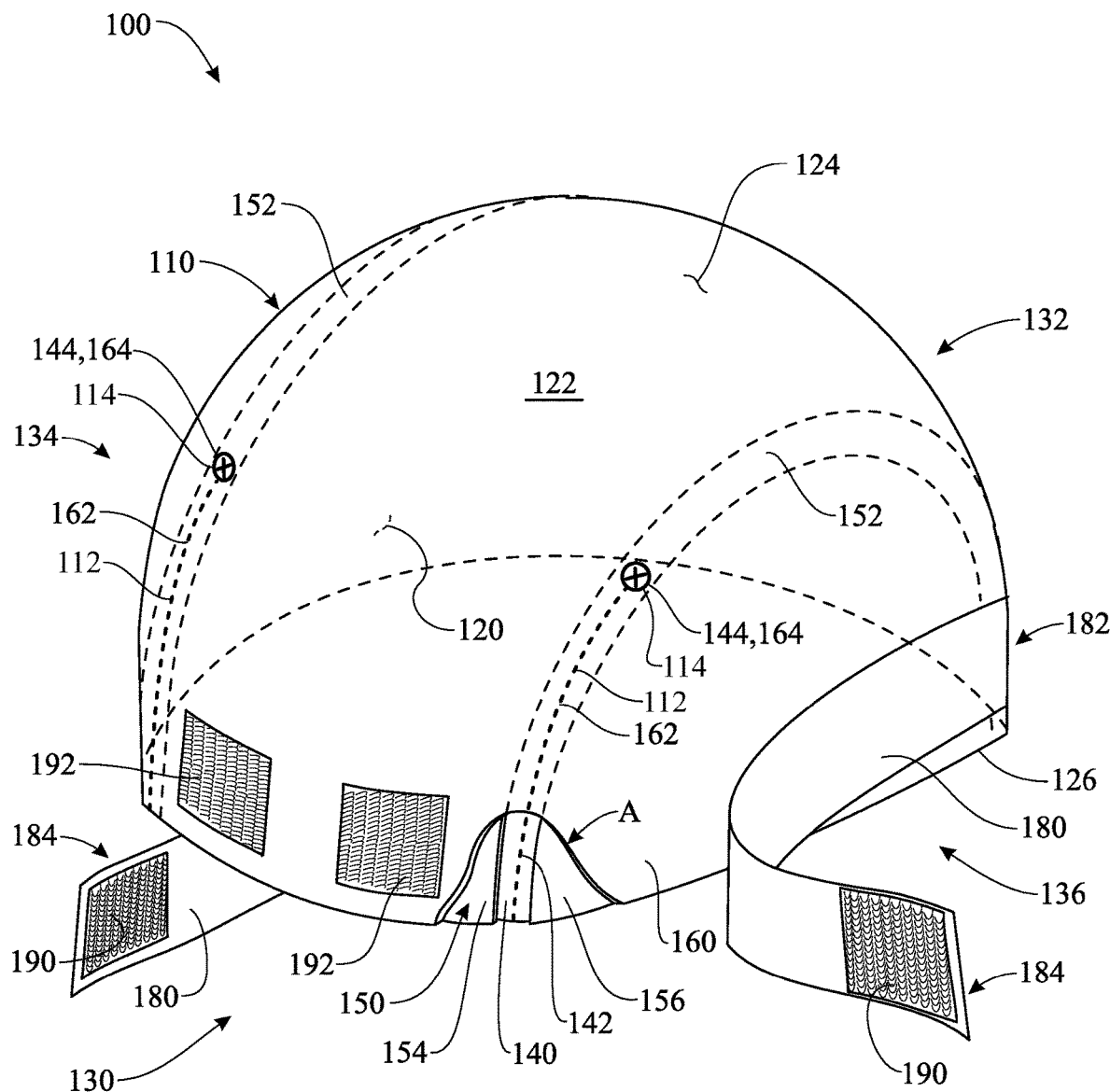
FIG. 1 presents a detailed perspective view of a first exemplary medical bandage in accordance with the invention, the view including an exemplary and imaginary cut-out portion for unveiling the otherwise concealed first and second layers.

The illustration of FIG. 1 presents a first exemplary embodiment of a medical bandage 100 in accordance with the invention. The medical bandage 100 comprises a main body 110 that is in shape of a cap. The main body 110 presents a concave, inner surface 120 delimiting a head-, limb- or stump-receiving cavity 122, and a convex, outer surface 124, where the inner and outer surfaces 120, 124 converge in a perimetric rim 126. The main body 110 further presents a front side 130, a rear side 132, a right side 134 and a left side 136.

Figure 6:
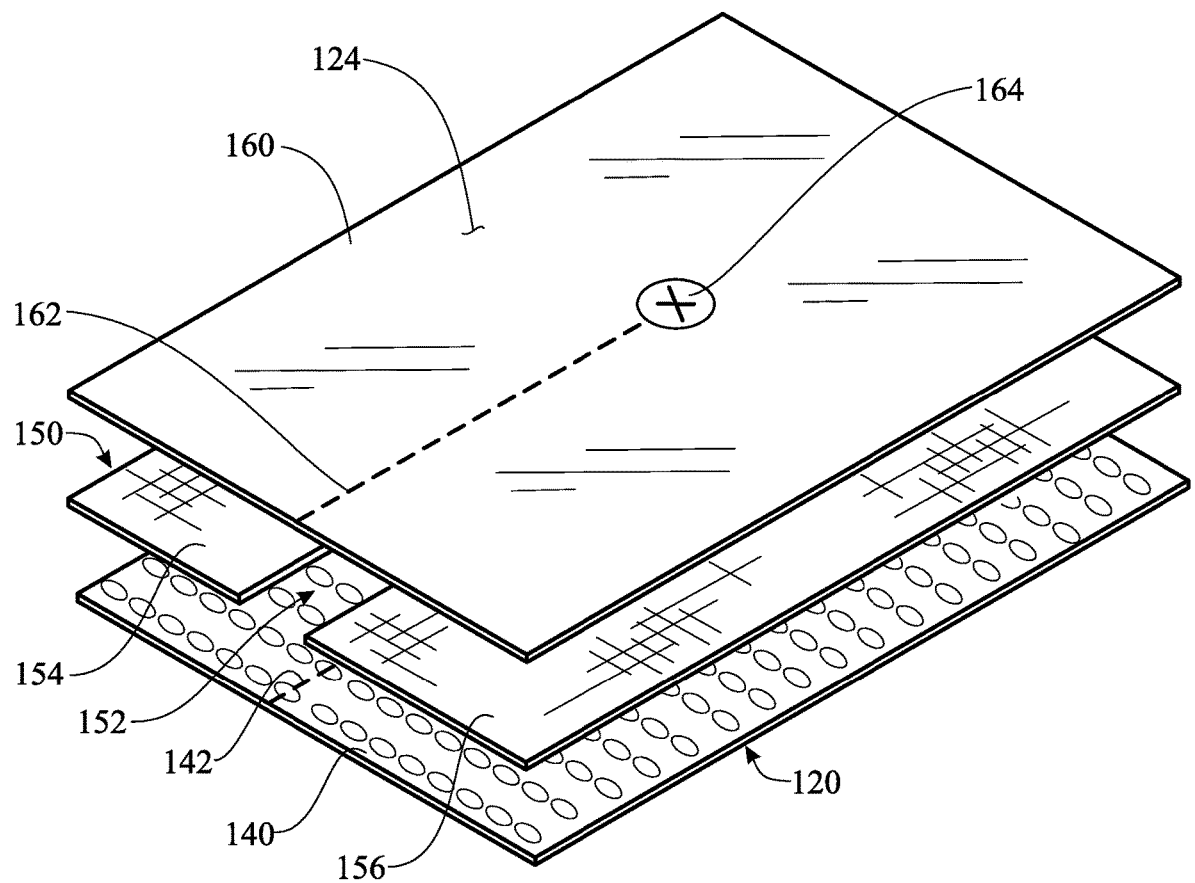
FIG. 6 presents an enlarged perspective view of the layers comprised in the medical bandage of FIG. 1.

Several layers and materials form the main body 110, namely a skin-compatible first layer 140, an absorbent second layer 150, and a breathable, non-permeable third layer 160, as shown in the general perspective view of FIG. 1 and in the enlarged, exploded view of FIG. 6. The first layer 140 and second layer 150 can be manufactured, for instance, from cloth, gauze, cotton, polyurethane, or a combination thereof. The third layer 160 can be manufactured, for instance, as a polyethylene film. For better understanding of the layered arrangement, an illustrative and imaginary cut-out (indicated with letter A) has been carried out in the third layer 160 of FIG. 1, unveiling the inner first and second layers 140, 150. As shown, the first layer 140 is arranged closer to the inner surface 120; in the present embodiment, in particular, the first layer 140 is in fact the innermost layer, and thus the innermost surface of the first layer 140 provides the main body inner surface 120. In turn, the third layer 160 is arranged closer to the outer surface 124; in the present embodiment, in particular, the third layer 160 is in fact the outermost layer, and the outermost surface of the third layer 160 provides the main body outer surface 124. The second layer 150 is arranged between the first layer 140 and the third layer 160; the second layer 150 of the present embodiment is, in fact, arranged immediately between the first layer 140 and the third layer 160. Thus, the main body in accordance with the invention can comprise three or more layers, the main body 110 of the present embodiment specifically consisting of three layers 140, 150, 160. In addition, the first layer 140 is permeable to the passing of fluid from the inner surface 120 towards the absorbent second layer 150, while the non-permeable third layer 160 keeps liquids and optionally gasses within the absorbent second layer 150. All layers 140, 150, 160 can have a variable thickness. The first and second layers 140, 150 can have a variable permeability and absorbency. The second layer 150, in particular, can be manufactured having different thicknesses in order to provide a variable degree absorbency and cushioned feel and wound-healing properties.

As shown in FIG. 1, the medical bandage 100 can further include one or more adjustment straps 180, each configured to adjustably attach to two different sections or zones of the main body 110, and provide compression if needed. The one or more straps can be arranged in a variety of directions. In the present embodiment, for instance, the medical bandage 100 includes two straps 180, wherein each strap 180 is arranged from the main body rear side 132 to the main body front side 130, extending along the right side 134 and left side 136, respectively. Being able to adjust the level of tightness with which the two straps 180 are attached allows adjusting the size of the cap-shaped main body 110 to different head, limb or stump sizes, and applying needed pressure or coverage to help stop bleeding, keep the bandage secure, and protect the wound, thereby promoting wound healing and assisting in post trauma/surgical care.

In the present embodiment, a first end 182 of the adjustment straps 180 is fixedly or non-disconnectably attached to the main body rear side 132 and an opposite second end 184 is disconnectably attachable to the main body front side 130. Thus, the straps 180 are permanently attached to the main body 110, preventing the straps 180 from being inadvertently lost when their second end 184 is detached from the main body 110, and yet are easily and rapidly detachable to readjust the fitting of the cap on a head or limb.

In the present embodiment, the straps 180 are disconnectably attachable to the main body 110 by a hook-and-loop connection formed by a first hook-and-loop element 190 forming part of the strap 180 and a compatible second hook-and-loop element 192 included in the main body 110 and configured to attach to the first hook-and-loop element 190. A hook-and-loop connection is advantageous in that it is easy and rapidly connected and disconnected, provides a secure and resistant attachment, and is a cost-effective solution. In addition, it can be easily and rapidly tightened in the event that a greater pressure (or even a tourniquet effect) is required on the wound; similarly, the hook-and-loop connection can be easily and rapidly loosened in the event that an excessive pressure is being applied that is causing discomfort in the patient.

Furthermore, the straps 180 of the present embodiment are arranged to extend along the right side 134 and left side 136, respectively, generally along the rim 126 and parallel to the rim 126. Thus, when the straps 180 are relatively tightly fastened to provide a snug fitting of the cap onto the patient's head or limb, the straps 180 provide a uniform pressure along a substantial length of the rim 126. In consequence, the adjusted bandage 100 is very safely secured and yet does not cause discomfort to the patient.

Alternative embodiments of the invention can comprise a different number of straps. In addition, in different embodiments of the invention, one or more straps can have both opposite ends disconnectably attachable to different sections of the main body, instead of having one end permanently affixed to the main body. In further embodiments, the main body can be at least partially elastic to adjustably fit onto a head, a limb or a stump. For instance, the first and/or third layers 140, 160 could be provided with an elastic band along the cap-shaped main body rim 126 so that the area of the rim 126 tightly (but comfortably) adjusts to the head, limb or stump while the rest of the main body 110 is more loosely fitted. In another example, the entire first layer 140 and/or third layer 160 can be elastic, to provide a compressive effect on the head, limb or stump that can be convenient for stopping wound bleeding or other applicable medical needs. In general, it is contemplated that the bandage 100 can be configured to snugly fit onto the head, limb or stump, in order for the first layer 140 to contact the wound, or to be more loosely arranged so that the first layer 140 does not contact the wound.

The bandage in accordance with the invention includes at least one port providing selective access to the cavity from outside the bandage. A nurse or other medical professional can thus easily insert a needle, tube or other medical device through the port, without having to reposition or remove the bandage from the patient's head or limb. A tube can be supported by a port, or repositioned from one port to another, without requiring the use of tape. For example, the present embodiment provides two elongated through ports 112 and two punctual or discrete through ports 114. The discrete through ports 114 allow for a rapid and adjusted insertion of the syringe or tube at specific, predetermined spots. The elongated through ports 112, instead, allow the medical professional to select where along the elongated port 112 to insert the syringe or tube, permitting a more versatile and personalized treatment.

The elongated through ports 112 of the present embodiment are constructed by having the first and third layers 140, 160 include two respective scored or perforated elongated seams 142, 162 arranged aligned or in registration and that can be quickly and rapidly torn or opened in order to apply a medicine onto, disinfect or treat a wound, or visually inspect the wound; the second layer 150 can comprise a similar scored or perforated seam in registration with the elongated seams 142, 162 of the first and third layers 140, 160 or, alternatively, as shown in FIG. 1, the second layer 150 can include two respective elongated channels or spaces 152 through which the first and third layers 140, 160, and more particularly elongated seams 142, 162, face each other directly.

In turn, the discrete through ports 114 are formed by two respective aligned perforated openings 144, 164 located at the end of the perforated seams 142, 162 of the first and third layers 140, 160 and in registration with the corresponding space 152 of the second layer 150. One or both openings 144, 164 can be scored or perforated X-cut openings, as shown, or present any other applicable shape such as an O-shape. In addition, alternative embodiments are contemplated such as having aligned openings on all three layers 140, 150, 160. It is also contemplated that an opening on the outer, third layer 160 can be initially closed or sealed and only accessible therethrough when ripped or perforated, while an opening on the first and/or second layer 140, 150 can be initially open and readily accessible once the opening on the third layer 160 is ripped or perforated.

Figure 2:
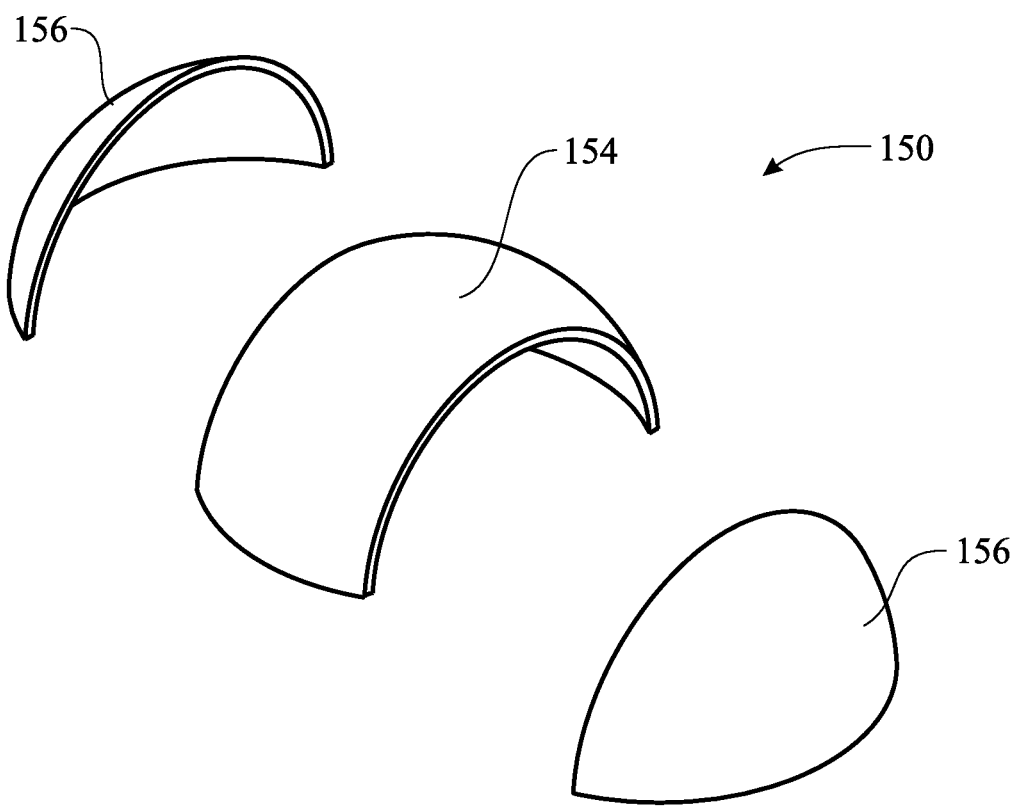
FIG. 2 presents an exploded view of the second layer, showing the partial portions forming the layer.
Figure 3:
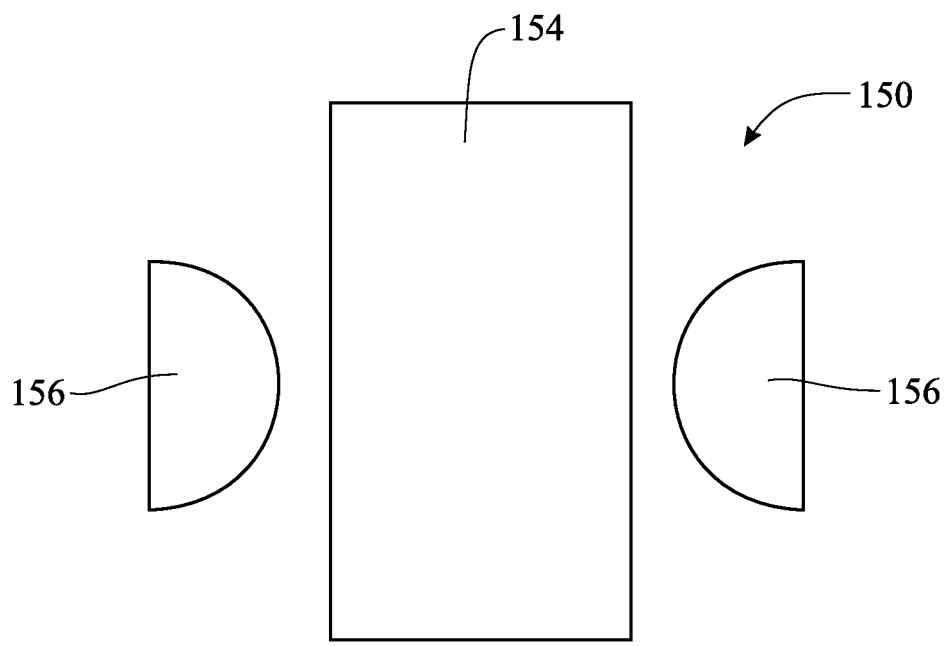
FIG. 3 presents a top plan view of the partial portions of FIG. 2.

Preferably, any one of the first layer 140, the second layer 150 and the third layer 160 can be formed of a plurality of partial portions, arranged adjacent to one another in order for the layer to adopt a three-dimensional cap shape. For instance, as best shown in FIGS. 2 and 3, the second layer 150 of the present embodiment is formed by one longitudinal partial portion 154, which is configured to extend form a frontal area to an occipital area, and two separate opposite side partial portions 156. Such a construction is cost effective as it utilizes a minimum amount of flat-shaped partial portions (as best shown in FIG. 3) to build a three-dimensional cap-shaped second layer 150. The longitudinal partial portion 154 is rectangular, and the opposite side partial portions 156 are semicircular, all of which being simple shapes that may be manufactured at reasonable cost.

As can be observed in FIG. 1, the present embodiment is such that the elongated spaces 152 of the second layer 150 are carried out as respective gaps that have been left between adjacent partial portions 154, 156. Thus, perforation of the second layer partial portions 154, 156 manufacturing the product is avoided, and the cost of manufacture is kept reasonable. The three partial portions 154, 156 of the second layer 150 are kept in place by the first and third layers 140, 160. Optionally, an adhesive, stitching, scoring or the like can be applied to further maintain the relative position of the three layers 140, 150, 160. Any seams can be constructed so that they can be relatively easily torn, allowing for easy dressing changes.

The absorbent, second layer 150 can further include at least one coagulant agent, such as clay-based coagulants (kaolin, chitosan, talc), synthetic coagulants (e.g., polymers), animal-based coagulants (e.g., gelatins), plant-based coagulants (e.g., cellulose) or a combination thereof, preferably embedded in the absorbent layer material or applied on the absorbent layer material. In such an event, the first layer 140 is configured to be permeable for the outward passing of the coagulant agent towards the main body inner surface 120 and the cavity 122. In alternative embodiments, at least one coagulant agent can be included in the first layer 140, in closer proximity to the wound.

Alternatively or additionally, the absorbent second layer 150 can include at least one antimicrobial agent, such as zincs or silvers, in order to prevent bacterial, fungal or parasite infection of the wound. The antimicrobial agent is preferably embedded in the absorbent layer material or applied on the absorbent layer material. The first layer 140 can then be permeable for the outward passing of the antimicrobial agent towards the main body inner surface 120 and the cavity 122. In alternative embodiments, at least one antimicrobial agent can be included in the first layer 140, in closer proximity to the wound.

The absorbent second layer 150 can include at least one heating (exothermic) agent and/or at least one cooling (endothermic) agent, such as a metal oxide, ureas, citric acid, bicarbonates or a combination thereof, in order to prevent heat loss from the head, limb or stump. The heating agent and/or cooling agent is preferably embedded in the absorbent layer material or applied on the absorbent layer material. The first layer 140 can be permeable for the passing of the at least one heating agent and/or cooling agent through the first layer 140 and towards the main body concave, inner surface 120 and the cavity 122. In alternative embodiments, at least one heating agent and/or cooling agent can be included in the first layer 140, in closer proximity to the wound.

Alternatively or additionally, the bandage 100 can include an insulating material such as, but not limited to, biaxially-oriented polyethylene terephthalate (e.g., Mylar®). Alternatively or additionally, the bandage 100 can include adhesive and/or petroleum.

In some embodiments, the medical bandage is packaged clean and sterile and intended for single use only, whereas in other embodiments the medical bandage is a multi-use, washable bandage which can be subjected to cleaning and sterilization.

In summary, the invention provides a cap-shaped bandage capable of being fitted on a head, a limb or a stump, and even onto a toe, a finger, a sexual organ or other appendage of the human or animal body, comprising an inner skin-compatible layer capable of allowing body fluids from the wound to pass through, an intermediate absorbent layer capable of absorbing the body fluids, and an external breathable non-permeable layer for concealing the absorbent layer, retaining fluids within the absorbent layer and providing a clean finish to the bandage. In addition, the cap-shaped bandage includes at least one port for accessing the bandage inner cavity from the outside. The medical bandage 100 may be efficacious for a variety of therapeutic functions, including, without limitation, stemming the flow of body fluids, absorbing body fluids, easing pain, debriding the wound, protecting from infection, promoting healing, and reducing psychological stress.

Figure 4:
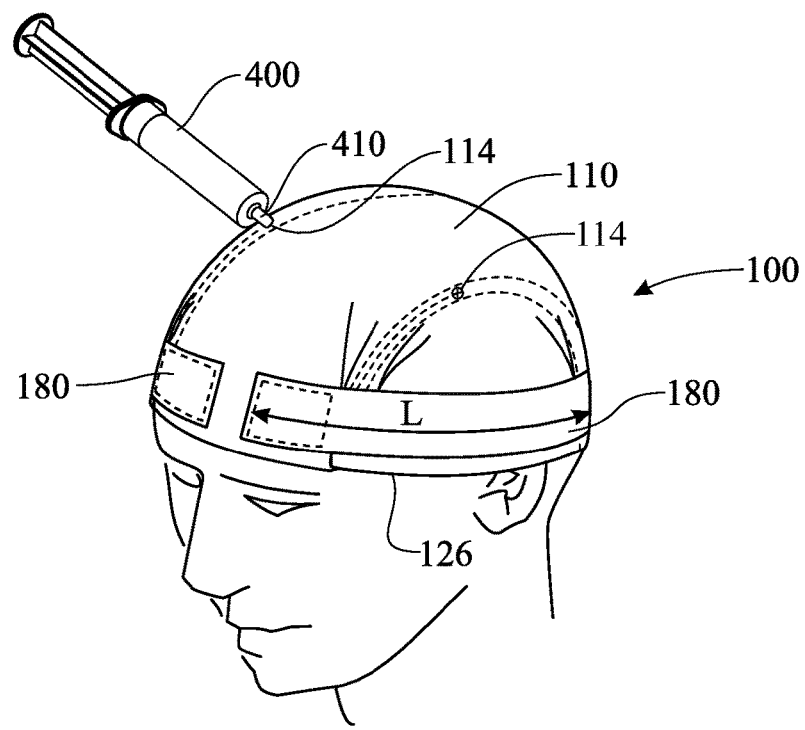
FIG. 4 presents a perspective view of the exemplary medical bandage of FIG. 1 fitted onto a person's head, and a syringe being applied onto a discrete port of the bandage in order to inject a medicine into the internal cavity of the bandage.

For instance, the illustration of FIG. 4 shows the bandage 100 applied on a patient's head, wherein the straps 180 have been tensioned and fastened to provide a lateral adjustment of the main body 110 against the periphery of the head, over the ears. As shown, the straps 180 extend along either side of the head in a generally symmetrical fashion, along and parallel to the rim 126, providing a snug adjustment of the cap. Since the straps 180 achieve a uniform pressure along a respective substantial length L, the straps 180 create no pressure points and cause no added discomfort to the patient. In addition, a syringe 400 has been inserted through one of the discrete through ports 114 by passing the syringe tip 410 through the opening 164 of the third layer 160, the corresponding elongated space 152 of the second layer 150 and the corresponding opening 144 of the first layer 140. Operation of the syringe 400 causes a medicine contained in the syringe 400 to be delivered directly into the cavity 122 and onto a wound without having to move the bandage 100 to a different position on the patient's head or without having to partially or completely remove the bandage 100 from the patient's head.

Figure 5:
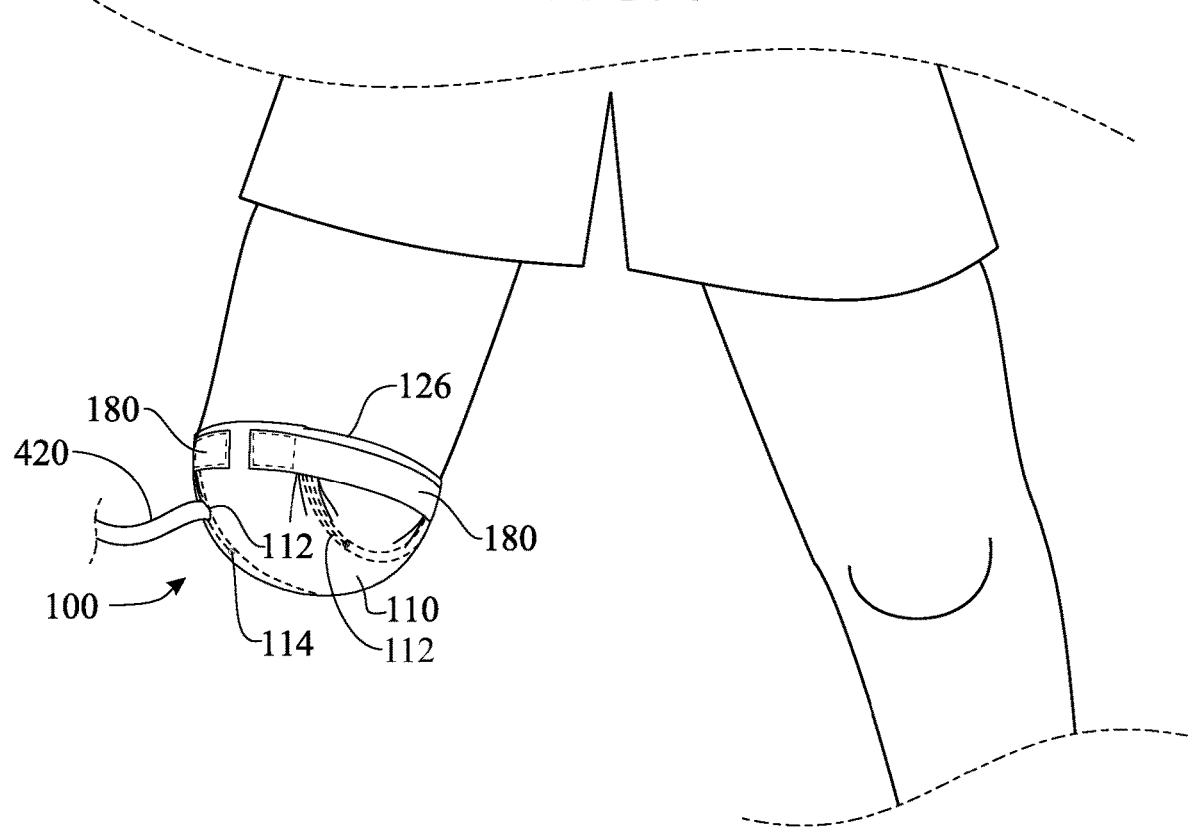
FIG. 5 presents a perspective view of the exemplary medical bandage of FIG. 1 fitted onto an amputated limb, having inserted a drainage tube through an elongated through port formed by partially opening aligned perforated seams providing selective access to the bandage internal cavity.

The illustration of FIG. 5 shows the bandage 100 placed covering a stump, where placement is again carried out by correctly positioning the cap-shaped main body 110, and tightening and attaching the straps 180 along and parallel to the rim 126. The medical professional has further inserted a drainage tube 420 through one of the elongated through ports 112, which has been previously formed or opened by tearing a length of the perforated seams 142, 162 of the first and third layers 140, 160 in order to open a passageway through the opened seams 142, 162 and the elongated space 152. Direct access to a wound in order to remove body fluids from the wound is therefore achieved without having to re-position or remove the bandage 100, thus preventing further discomfort to the patient.

Therefore, a single device is provided that can be intuitively and universally used to cover either a wound on the head or a wound on a stump. In addition, the device is extremely easy and convenient to use, saving precious medical treatment time and allowing a more rapid care of severe wounds, and ongoing treatment of chronic wounds. Being able to dress a wound more rapidly is greatly beneficial for the patient, as bleeding can be controlled much sooner by means of the immediate stop effect provided by the direct placement of the bandage; in addition, the wound exposure time is cut down, thereby reducing the risk of infection.

Figure 7:
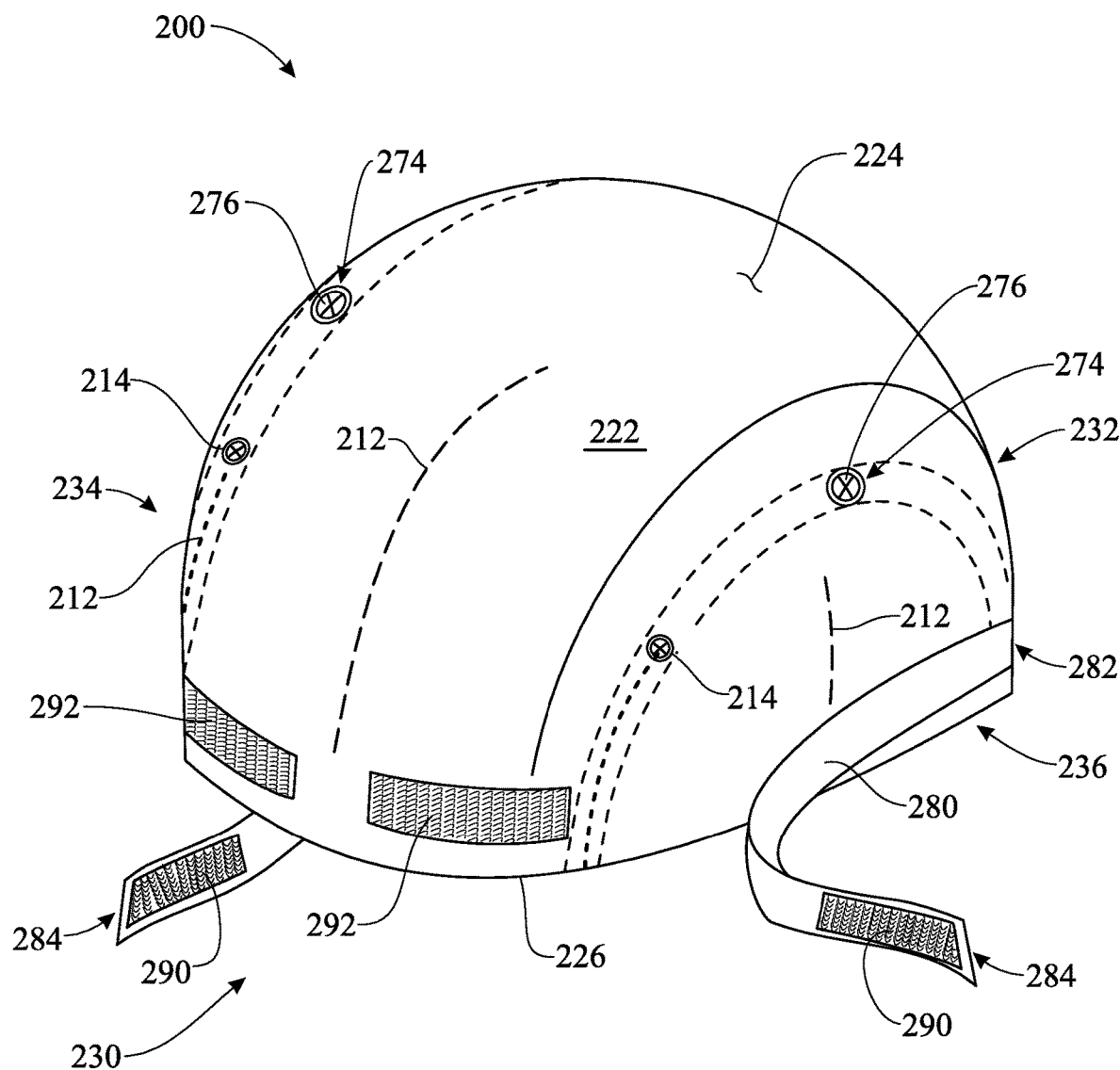
FIG. 7 presents a detailed perspective view of a second exemplary medical bandage in accordance with the invention.

The illustrations of FIGS. 7 through 10 present a bandage 200 in accordance with a second exemplary embodiment of the invention. Like features of the bandage 200 of FIGS. 7 through 10 and the bandage 100 of FIGS. 1 through 6 are numbered the same except preceded by the numeral '2'. As in the previous embodiment, the bandage 200 comprises a main body 210 having a front side 230, a rear side 232, a right side 234, a left side 236, an inner surface 220, an outer surface 224, an internal cavity 222 for receiving a head or stump, and a bottom edge or rim 226 delimiting a bottom opening for inserting the head or stump into the cavity 222. The main body 210 further includes several elongated through ports 212 and two punctual or discrete through ports 214 providing access to the internal cavity 222 from outside the bandage 200. Two straps 280 extend from the rear side 232 to the front side 230 of the main body 210, along the left and right sides 236, 234, respectively, and along the rim 226 and parallel to the rim 226. Similarly to the previous embodiment, a first end 282 of the adjustment straps 280 is fixedly or non-disconnectably attached to the main body rear side 232 and an opposite second end 284 is disconnectably attachable to the main body front side 230. The straps 280 are disconnectably attachable to the main body 210 by a hook-and-loop connection formed by a first hook-and-loop element 290 forming part of the strap 280 and a compatible second hook-and-loop element 292 included in the main body 210. As shown in FIG. 7, the first and second hook-and-loop elements 290, 292 are elongated and arranged parallel to the rim 226, thereby increasing the adjustment range provided by the straps 280 and thus favoring that a single-size bandage 200 is usable on different head sizes or body parts.

Figure 8:
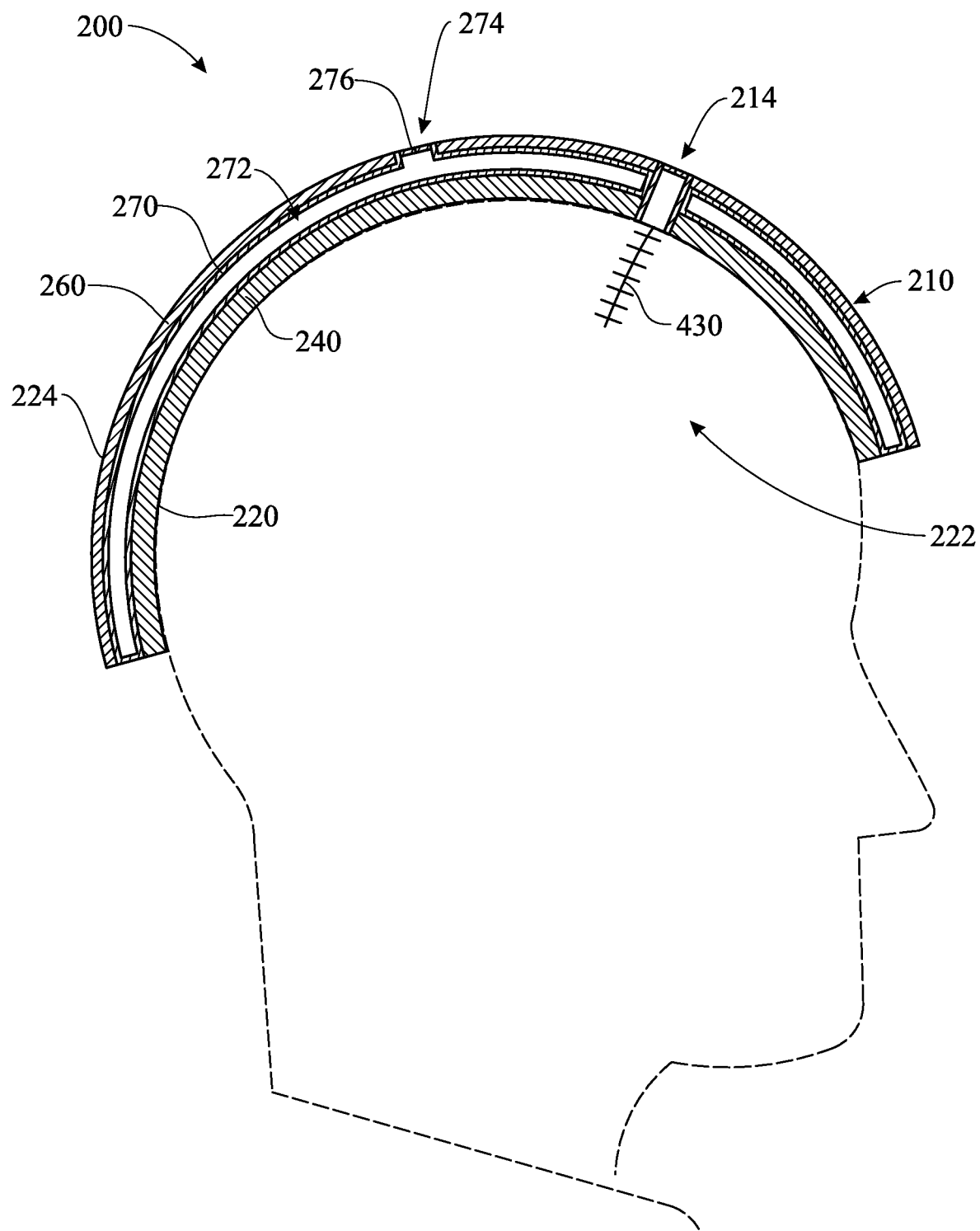
FIG. 8 presents a cross-sectional side elevation view of the medical bandage of FIG. 7 fitted onto a patient's head, in accordance with a first application in which the bandage is simply applied onto and adjusted to the head.

The main body 210 is formed of an innermost soft, skin-compatible first layer 240, an outermost non-permeable third layer 260, and an intermediate second layer. As shown in FIG. 8, the second layer of the present embodiment is a flexible bladder 270, i.e. a flexible non-permeable layer comprising an internal cavity 272 for housing at least one solid substance, at least one liquid substance, at least one gaseous substance, or combinations thereof. A bladder access port 274 provides access to the internal cavity 272, for instance in order to inject air or warm water into the internal cavity 272. The bladder access port 274 of the present embodiment is initially closed by a perforable or tearable membrane 276, which can optionally include an X-shaped score or other predefined score to facilitate tearing or perforating the membrane 276 with a syringe or manually, to name a few examples. In some embodiments, the internal cavity 272 can be provided with isolated or non-isolated compartments to promote a uniform distribution of the substance(s) within the cavity.

Figure 9:
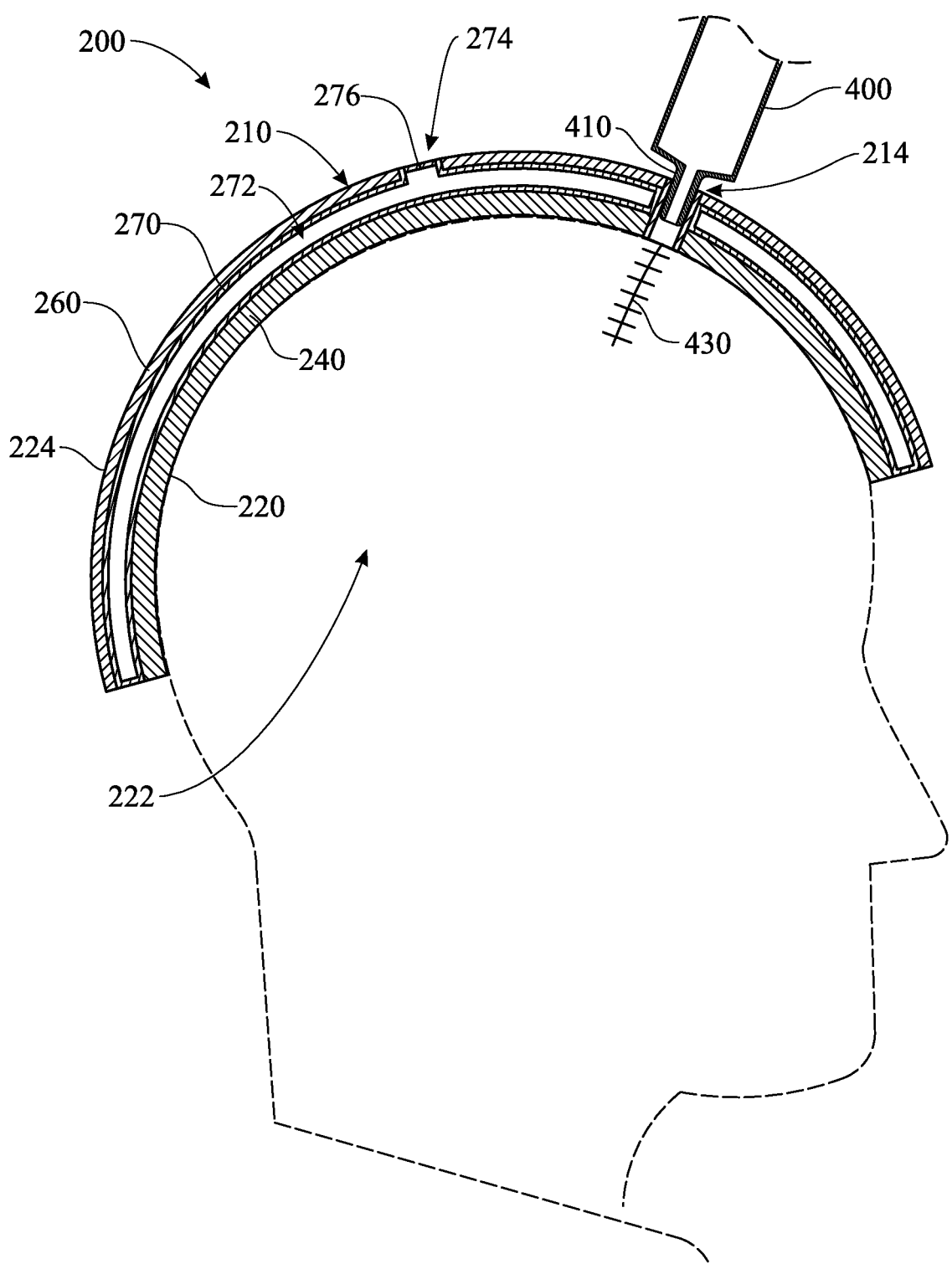
FIG. 9 presents a cross-sectional side elevation view of the medical bandage of FIG. 7 fitted onto a patient's head, in accordance with a second application, in which a syringe is inserted into a discrete through port in order to deliver a medicine to a wound on the head.
Figure 10:
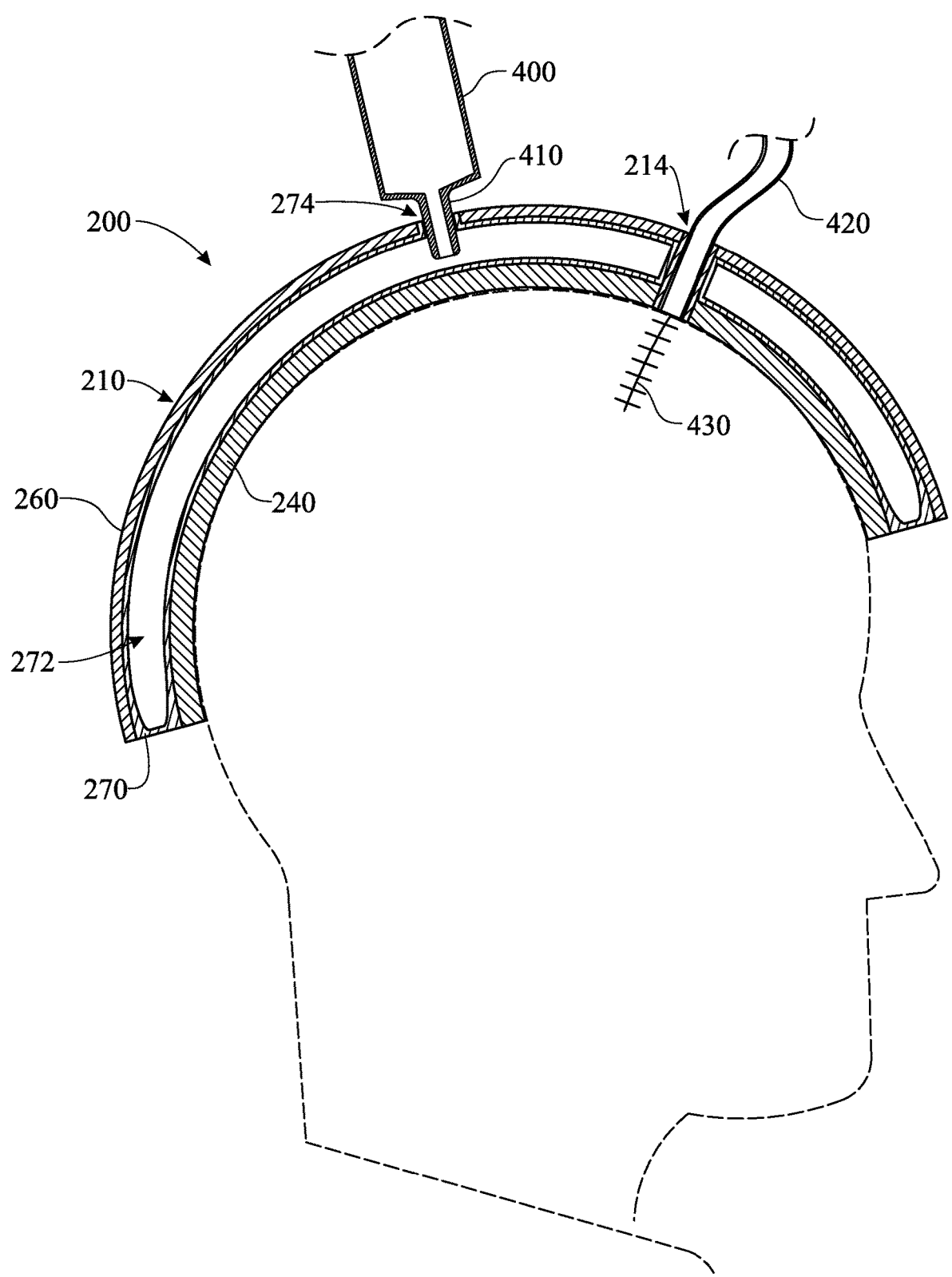
FIG. 10 presents a cross-sectional side elevation view of the medical bandage of FIG. 7 fitted onto a patient's head, in accordance with a third application, in which a syringe is inserted into a bladder access port to inject air or a liquid or solid medicament, and inflate the bandage to provide light compression to a wound, and a drainage tube is inserted into a discrete through port in order to remove body fluids from the wound.

The illustrations of FIGS. 8 through 10 depict several usage scenarios of the bandage of FIG. 7. Referring initially to FIG. 8, the bandage 200 is shown fitted onto a patient's head in order to provide an adjusted dressing of the head in the event of a trauma or wounds. The illustration of FIG. 9, in turn, shows the bandage 200 fitted onto a patient's head and a syringe 400 having perforated and penetrated a discrete through port 214 and in the process of administering a liquid medicine (not shown) onto a wound 430. Finally, the illustration of FIG. 10 presents a further application in which the bandage 200 has been fitted onto a patient's head and a nozzle or syringe 400 has perforated the membrane 276 (FIG. 8) and penetrated the bladder access port 274 and has injected air into the inner flexible bladder 270, causing the flexible bladder 270 to expand and the bandage 200 to compress the head of the patient, such as to stop bleeding of a wound 430. In turn, a drainage tube 420 has been inserted through a discrete through port 214 in order to remove body fluids from a wound 430. In a further application, not shown in the drawings, a vacuum tube could be inserted into a discrete through port 214 and a suction force could be applied through the vacuum tube in order to create a vacuum inside the bandage 200, thereby removing air from the internal cavity of the main body and thus reducing the risk of contamination of the wound as well as increasing compression of the wound.

In some embodiments, the internal cavity 272 of the flexible bladder 270 can hold solid substances for specific treatment purposes. For instance and without limitation, the bandage 200 can be manufactured in such a way that the internal cavity 272 is marketed containing solid substances that are configured to exothermically react with a liquid (e.g., water). Thus, when placing the bandage 200 on the patient's head or limb, the medical professional can inject water through the bladder access port 274 to cause an exothermic reaction between the water and the solid substances and thus warm the bandage 200.

Alternative embodiments are contemplated in which the main body includes both an internal flexible bladder and an internal absorbent layer, in which case the flexible bladder is preferably arranged externally to the absorbent layer. The main body is therefore capable of absorbing and retaining body fluids from a wound and simultaneously compressing the wound, for instance to stop the wound from bleeding.

Figure 11:
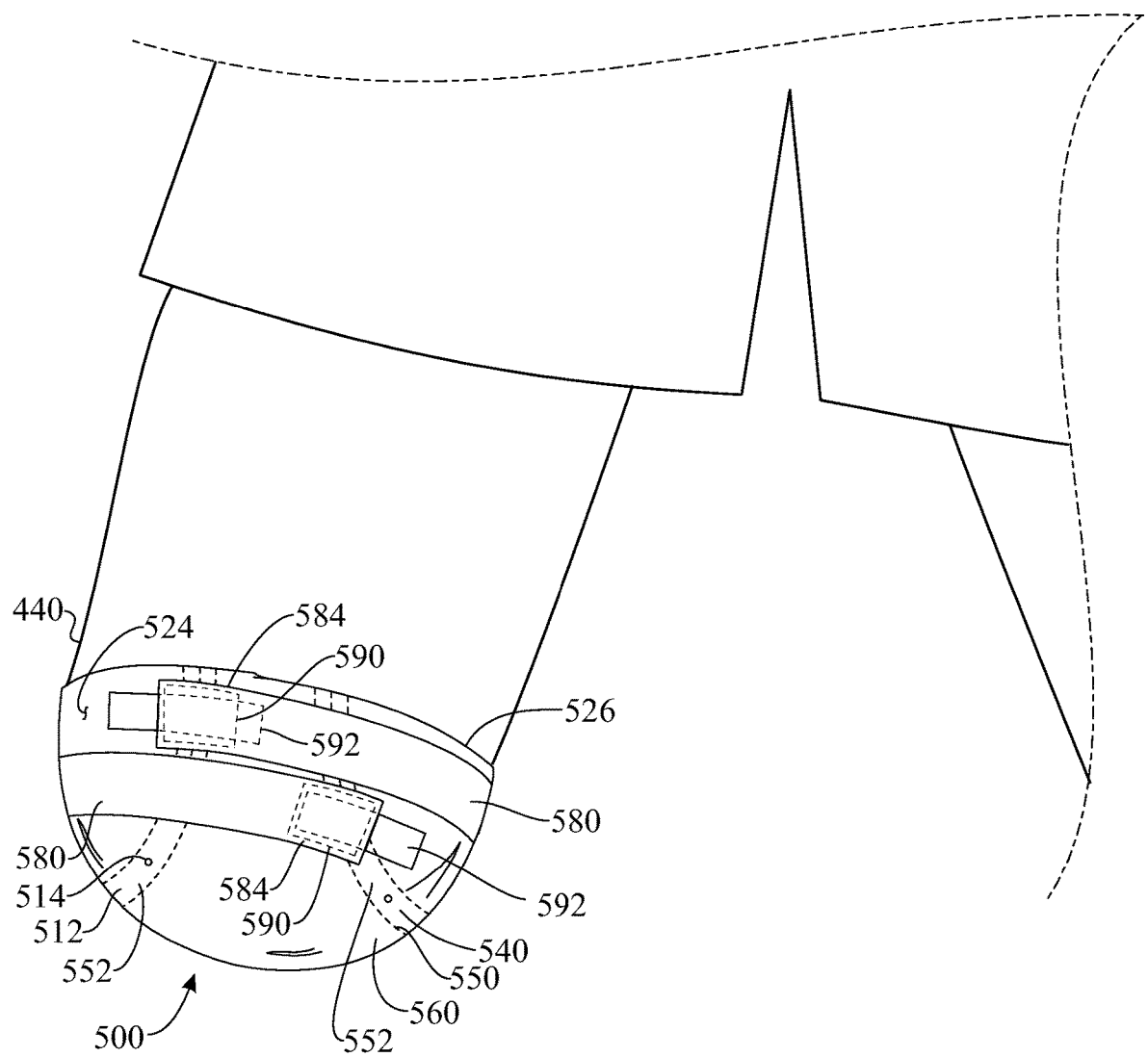
FIG. 11 presents a perspective view of a medical bandage in accordance with a third illustrative embodiment of the invention, showing the medical bandage applied to a leg stump with two straps securing the bandage in place.
Figure 12:
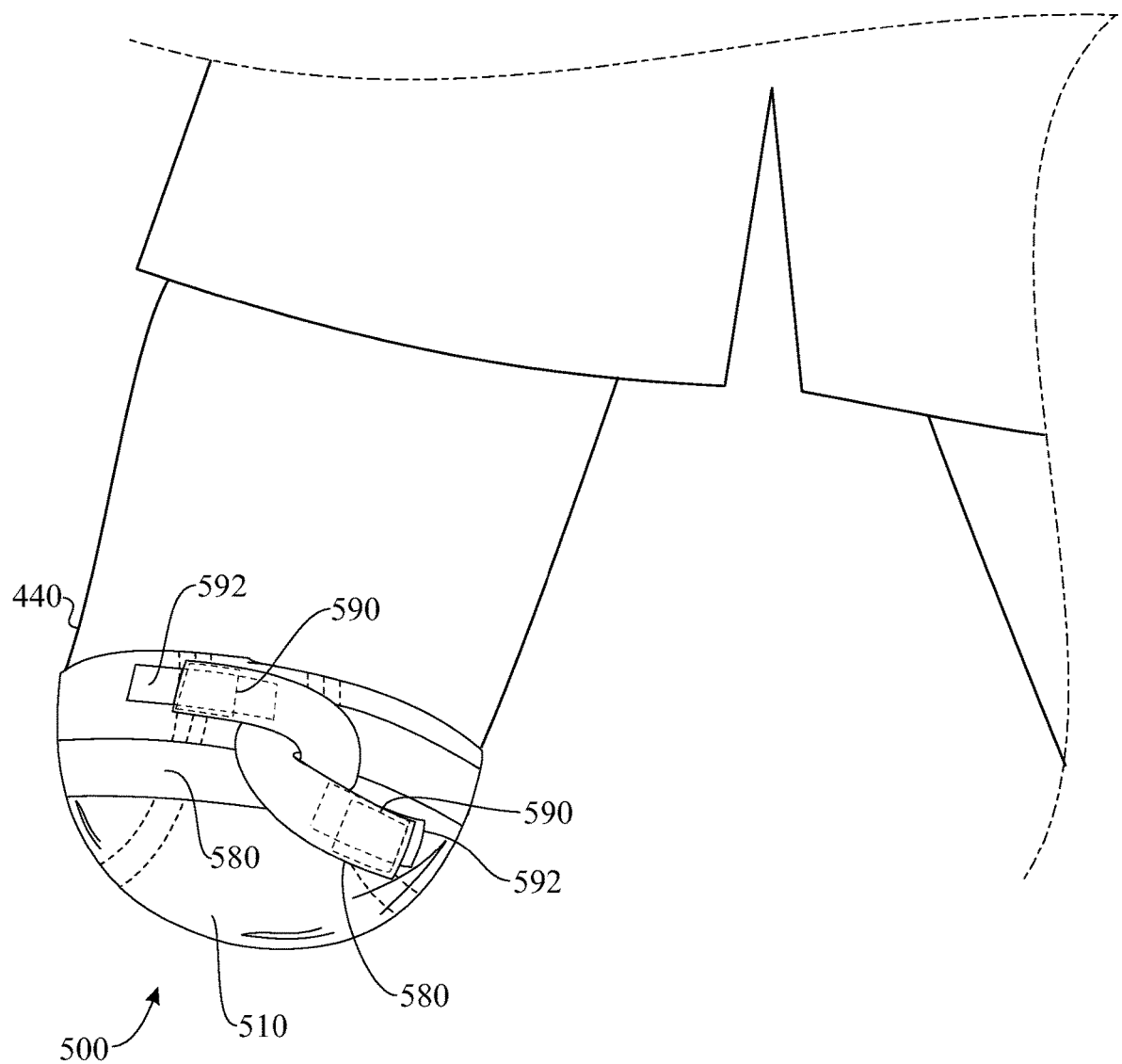
FIG. 12 presents an alternative use of the medical bandage of FIG. 11, in which the straps are wound to one another to further tighten the medical bandage onto the leg stump.
Figure 13:
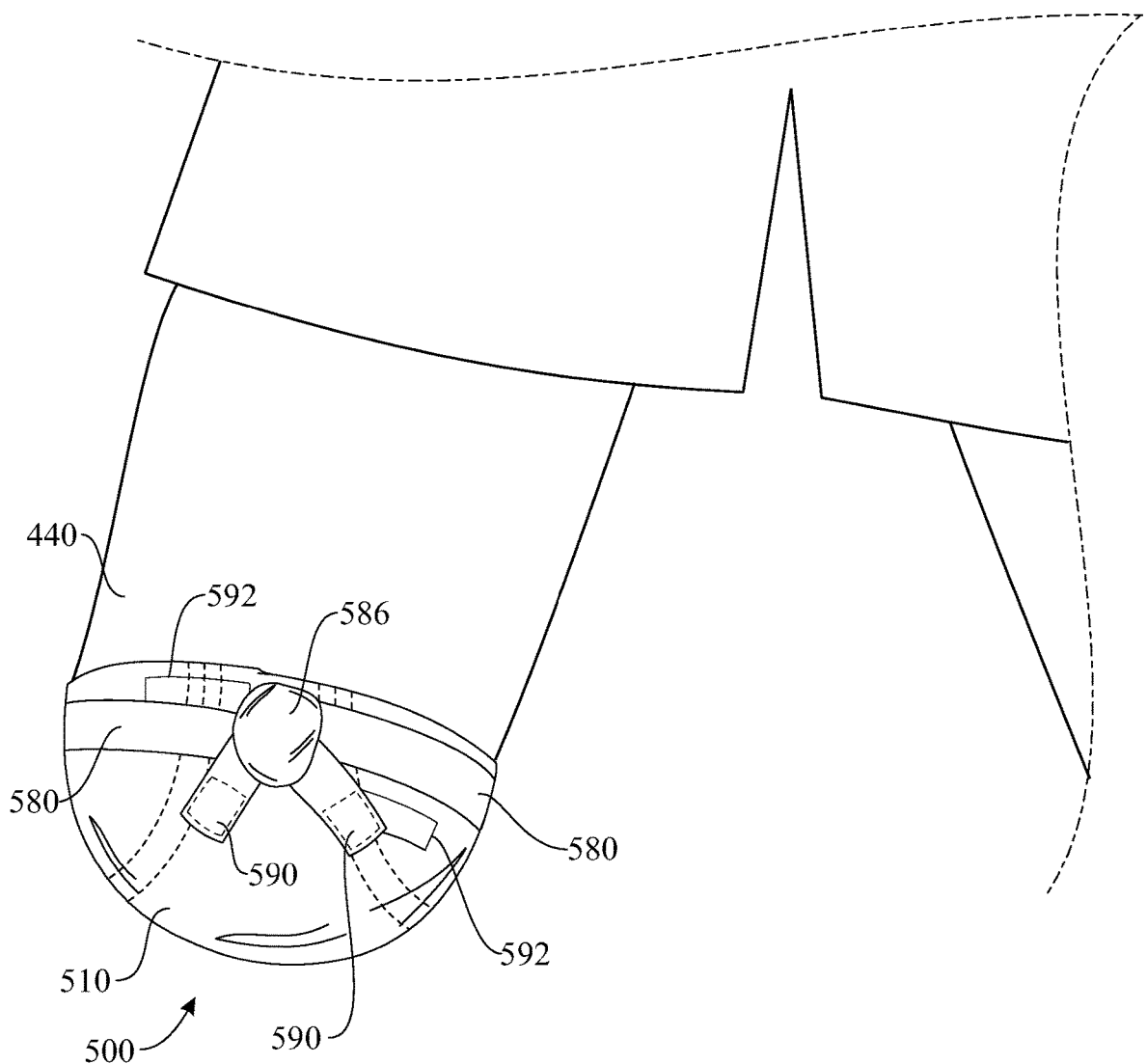
FIG. 13 presents yet another alternative use of the medical bandage of FIG. 11, with the straps tied into a knot to further tighten the medical bandage.

The illustrations of FIGS. 11 through 13 present a bandage 500 in accordance with a third exemplary embodiment of the invention. Like features of the bandage 500 of FIGS. 11 through 13 and the bandage 100 of FIGS. 1 through 6 are numbered the same except preceded by the numeral '5'. As shown, the bandage 500 comprises a cap-shaped main body 510. Similarly to previous embodiments, the main body 510 has an inner surface (not shown, but otherwise similar to inner surface 120 of bandage 100 shown in FIG. 1), an outer surface 524, and an inner cavity (not shown, but otherwise similar to inner cavity 120). The inner cavity is delimited by the inner surface and is configured to at least partially receive a head, limb, stump, finger or protruding body part. In the present figures, for instance, the bandage 500 is shown applied to a leg stump 440 such that an end of the leg stump 440 is received within the inner cavity of the main body 510. Similarly to previous embodiments, the main body 510 comprises a skin-compatible first layer 540, a second layer 550, and a non-permeable third layer 560. The first layer 540 is arranged closer to the inner cavity than the third layer 560, and the second layer 550 is sandwiched between the first layer 540 and the third layer 560 and comprises at least one space 552 through which the first and third layers 540, 560 directly face one another. Similarly to previous embodiments, at least one through port 512, 514 is arranged at said at least one space 552, for accessing the inner cavity of the main body 510 from outside the main body 510 and through the first, second and third layers 540, 550 and 560, or for stabilizing or supporting a drain or tubing passing through the port.

As further shown in FIG. 11, two straps 580 extend along opposite sides of the main body 510, at or near an edge or rim 526 of the main body 510. Similarly to previous embodiments, a first end (not shown) and an opposite second end 584 of the adjustment straps 580 are non-disconnectably and disconnectably attached to the main body 510, respectively. The second end 584 of the straps 580 is disconnectably attachable to the main body 510 by a hook-and-loop connection formed by a first hook-and-loop element 590 forming part of the strap 580 and a compatible second hook-and-loop element 592 included in the main body 510.

As shown in FIG. 11, the first and second hook-and-loop elements 590, 592 can be elongated and arranged at or near the rim 526.

In a first illustrative use of the bandage 500, as shown in FIG. 11, the straps 580 can be normally arranged to extend along the main body 510 and the first hook-and-loop element 590 of each strap 580 can engage with the corresponding second hook-and-loop element 592 on the main body 510, without the straps 580 engaging with each other. In a second illustrative use of the bandage 500, shown in FIG. 12, the straps 580 are wound or twisted with one another and the second end 584 of each strap 580 is oriented rearward, toward the corresponding fixed, first end of the strap 580, with the second ends 584 attached to the second hook-and-loop elements 592 on the main body 510. This second application allows for a tighter fitting of the bandage 500 onto the stump or other body part. In a third illustrative application of the bandage 500, shown in FIG. 13, the straps 580 are tied into a knot 586, providing an even tighter fitting of the main body 510 onto the stump or other body part. Though not specifically shown in FIG. 13, the first hook-and-loop elements 590 carried by the straps 580 can be optionally attached to the second hook-and-loop elements 592 on the main body 510.

In other words, the straps of the present embodiment or other embodiments not only may present varying lengths but also are susceptible to being tied or arranged in different ways to provide various effects (e.g. varying-strength tourniquet effects) on the body part to be covered by the bandage.

Figure 14:
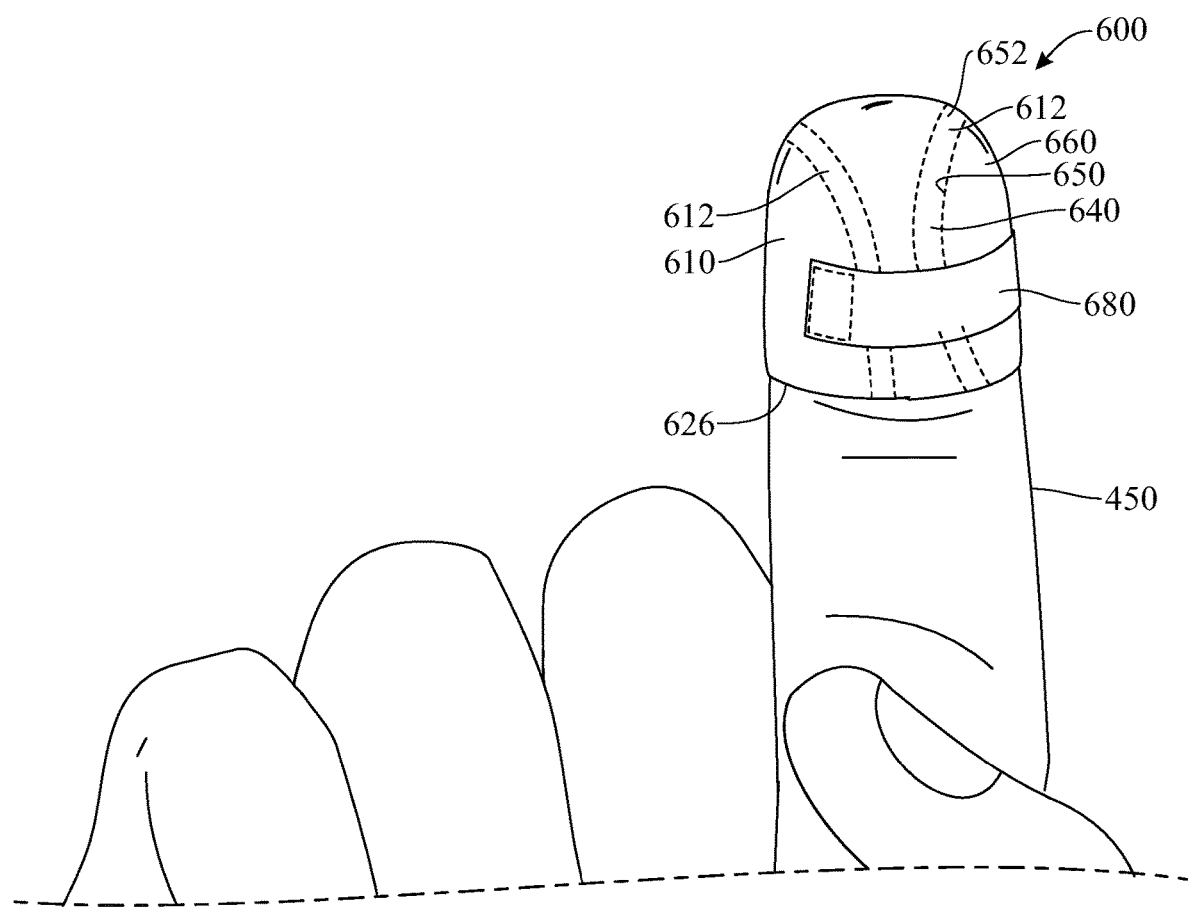
FIG. 14 presents a front view of a medical bandage in accordance with a fourth illustrative embodiment of the invention, wherein the medical bandage is shaped and sized to partially cover a finger.

The illustration of FIG. 14 presents a bandage 600 in accordance with a fourth illustrative embodiment of the invention. Like features of the bandage 600 of FIG. 14 and the bandage 100 of FIGS. 1 through 6 are numbered the same except preceded by the numeral '6'. As shown, the bandage 600 comprises a cap-shaped main body 610 having an inner surface (not shown, but otherwise similar to inner surface 120 of bandage 100 shown in FIG. 1), an outer surface 624, and an inner cavity (not shown, but otherwise similar to inner cavity 120) which is delimited by the inner surface. Similarly to previous embodiments, the main body 610 comprises a skin-compatible first layer 640, a second layer 650, and a non-permeable third layer 660. The first layer 640 is arranged closer to the inner cavity than the third layer 660, and the second layer 650 is sandwiched between the first layer 640 and the third layer 660 and comprises at least one space 652 through which the first and third layers 640, 660 directly face one another. Similarly to previous embodiments, at least one through port 612 is arranged at said at least one space 652, for accessing the inner cavity of the main body 610 from outside the main body 610 and through the first, second and third layers 640, 650 and 660, or for stabilizing or supporting a drain or tubing passing through the port. A single strap 680 extends along the main body 610, at or near an edge or rim 626 of the main body 610 and attaches to the main body 610 by a hook-and-loop fastener. The main body 610 of the present embodiment is, however, smaller in size than previous embodiments, and is configured to at least partially cover a user's finger 450.

Figure 15:
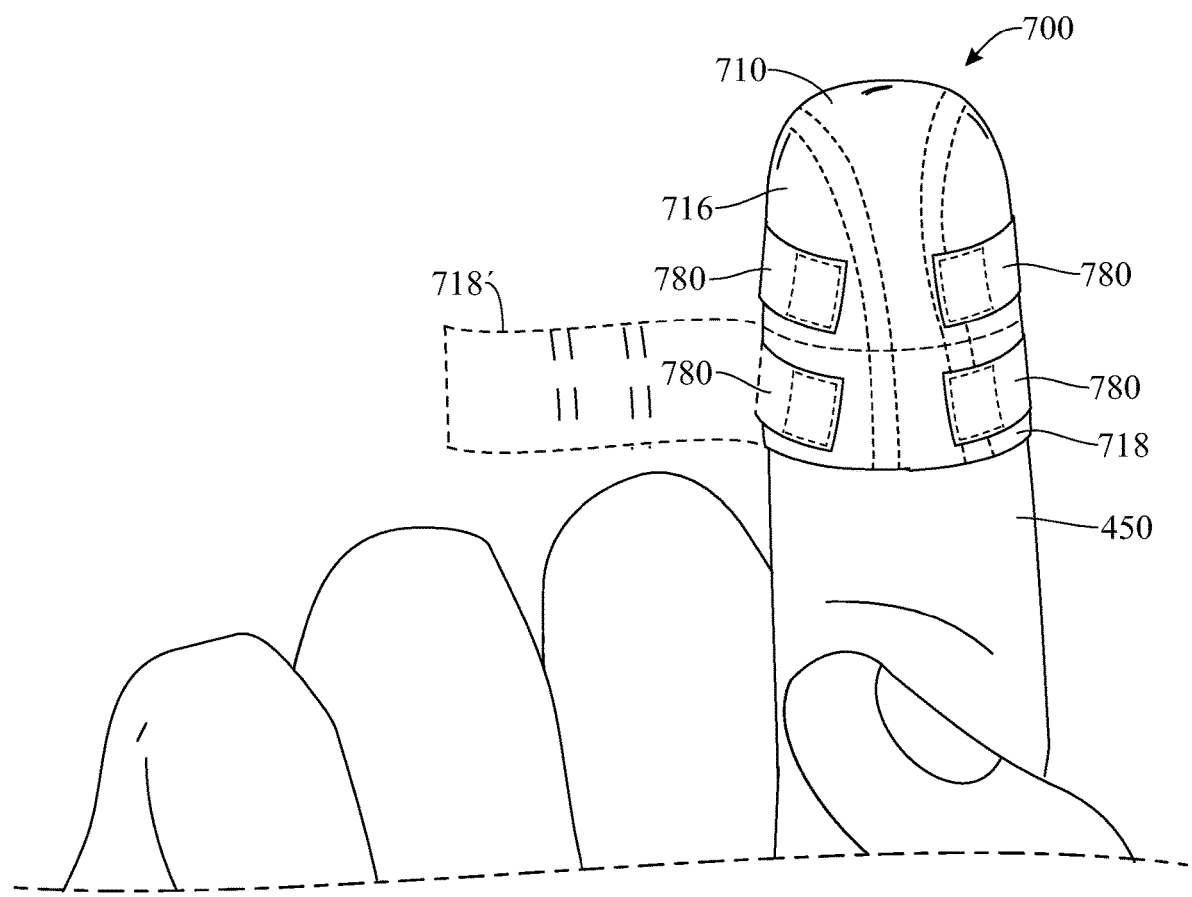
FIG. 15 presents a front view of a medical bandage in accordance with a fifth illustrative embodiment of the invention, wherein the medical bandage is shaped and sized to partially cover a finger and includes a removable bottom portion which can be separated to reduce the height of the medical bandage.

The drawing of FIG. 15 shows a bandage 700 in accordance with a fifth illustrative embodiment of the invention. Like features of the bandage 700 of FIG. 15 and the bandage 100 of FIGS. 1 through 7 are numbered the same except preceded by the numeral '7'. As shown, the bandage 700 comprises a cap-shaped main body 710 having an inner surface (not shown, but otherwise similar to inner surface 120 of bandage 100 shown in FIG. 1), an outer surface 724, and an inner cavity (not shown, but otherwise similar to inner cavity 120) which is delimited by the inner surface. Similarly to previous embodiments, the main body 710 comprises a skin-compatible first layer 740, a second layer 750, and a non-permeable third layer 760. The first layer 740 is arranged closer to the inner cavity than the third layer 760, and the second layer 750 is sandwiched between the first layer 740 and the third layer 760 and comprises at least one space 752 through which the first and third layers 740, 760 directly face one another. Similarly to previous embodiments, at least one through port 712 is arranged at said at least one space 752, for accessing the inner cavity of the main body 710 from outside the main body 710 and through the first, second and third layers 740, 750 and 760, or for stabilizing or supporting a drain or tubing passing through the port. At least one strap 780 extends along the main body 710, at or near an edge or rim 726 of the main body 710 and attaches to the main body 710 by a hook-and-loop fastener.

Similarly to the bandage 600 of FIG. 14, the main body 710 of the present embodiment is relatively small in size and is configured to at least partially cover a user's finger 450. In a further aspect of the invention, the bandage 700 of the present invention is provided with an adjustable height which allows a user to easily and conveniently alter the overall height of the main body 710, such as to adjust the main body 710 to different finger lengths, wounds or areas to be treated, etc. Specifically, the main body 710 can include several body portions which initially come attached to one another and can be separated from one another to reduce the size of the main body 710 if so required by the medical condition to be treated. For instance and without limitation, the main body 710 of the present embodiment includes comprises two body portions, i.e. a first body portion 716 and a second body portion 718. The first body portion 716 is cap-shaped and the second body portion 718 is annularly-shaped and extends along an edge of the first body portion 716. The first body portion 716 and second body portion 718 are initially attached to one another or integrally-formed with one another, with a scored or tear line or area 719 formed between the first and second body portions 716 and 718 to facilitate removing the second body portion 718 if not needed. In operation, the bandage 700 is placed on a person's finger 450 and, if the finger 450 is relatively long or the wound to be treated is relatively small and arranged at a tip of the finger, the second body portion 718 may be ripped or torn off the first body portion 716 along the tear area 719 and the second body portion 718 may be removed from the finger 450 and either discarded or used for alternative purposes (e.g. as a tourniquet). To illustrate this process of removing the second body portion 718, the drawing of FIG. 15 shows the second body portion 718 arranged in a partially removed position shown in broken lines and indicated with reference numeral 718'. As further shown in the drawing, one or both of the main body portions can be provided with one or more straps 780. The one or more straps 780 of the second body portion 718 are removable jointly with the second body portion 718. Furthermore, the at least one space 752 and corresponding through ports 712 can extend through one or both main body portions, in different implementations of the invention; for instance, in the example shown in the drawing, the spaces 752 and corresponding through ports 712 extend along both the first body portion 716 and the second body portion 718. Finally, it must be noted that, similarly to other aspects of the invention, the aspect of having the main body formed by two or more separable parts can be applied to any one of the other embodiments described herein.

Figure 16:
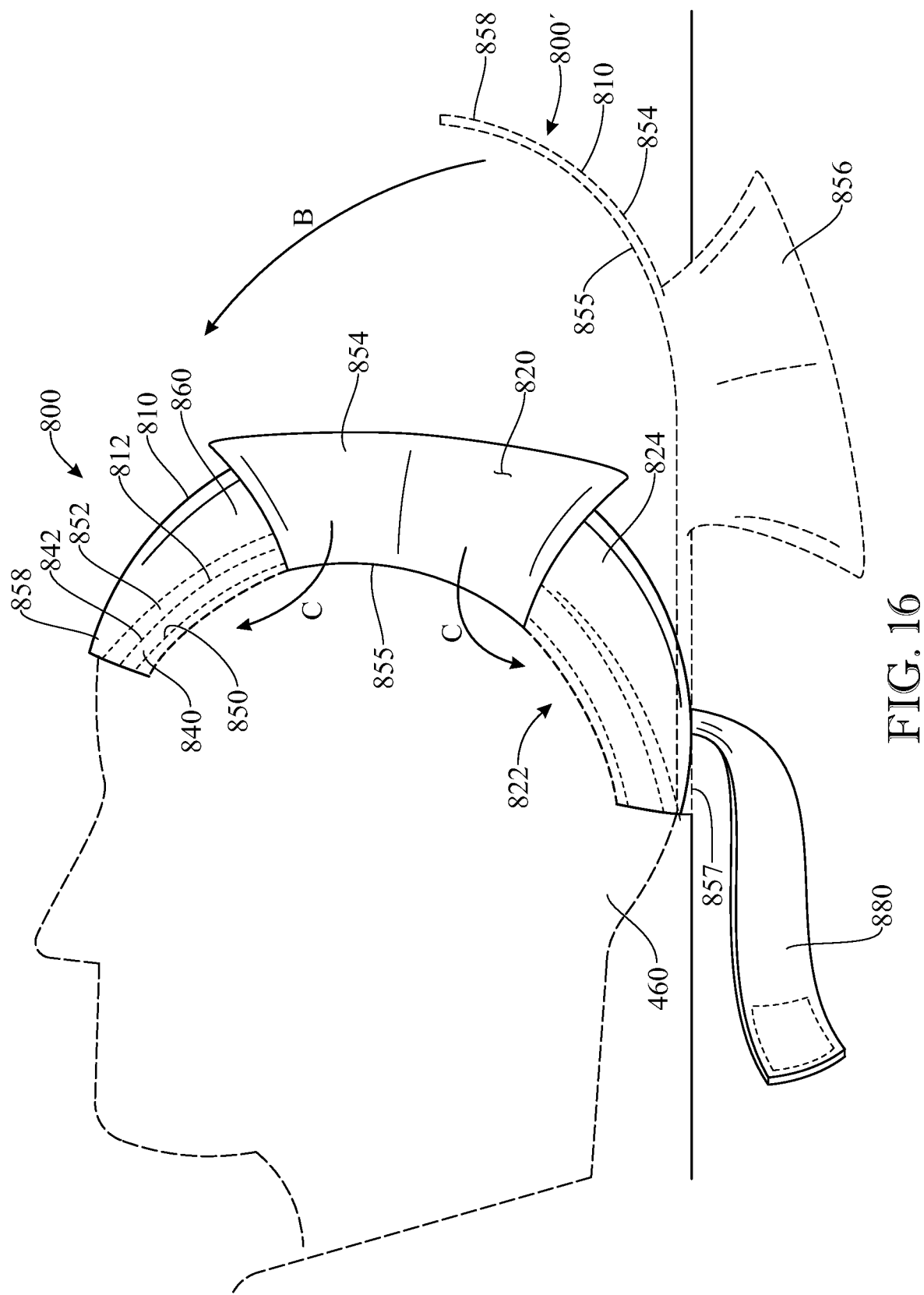
FIG. 16 presents a side view of a medical bandage in accordance with a sixth illustrative embodiment of the invention, wherein the main body includes two pivotable side portions being operated to facilitate fitting the medical bandage onto a person's head.
Figure 17:
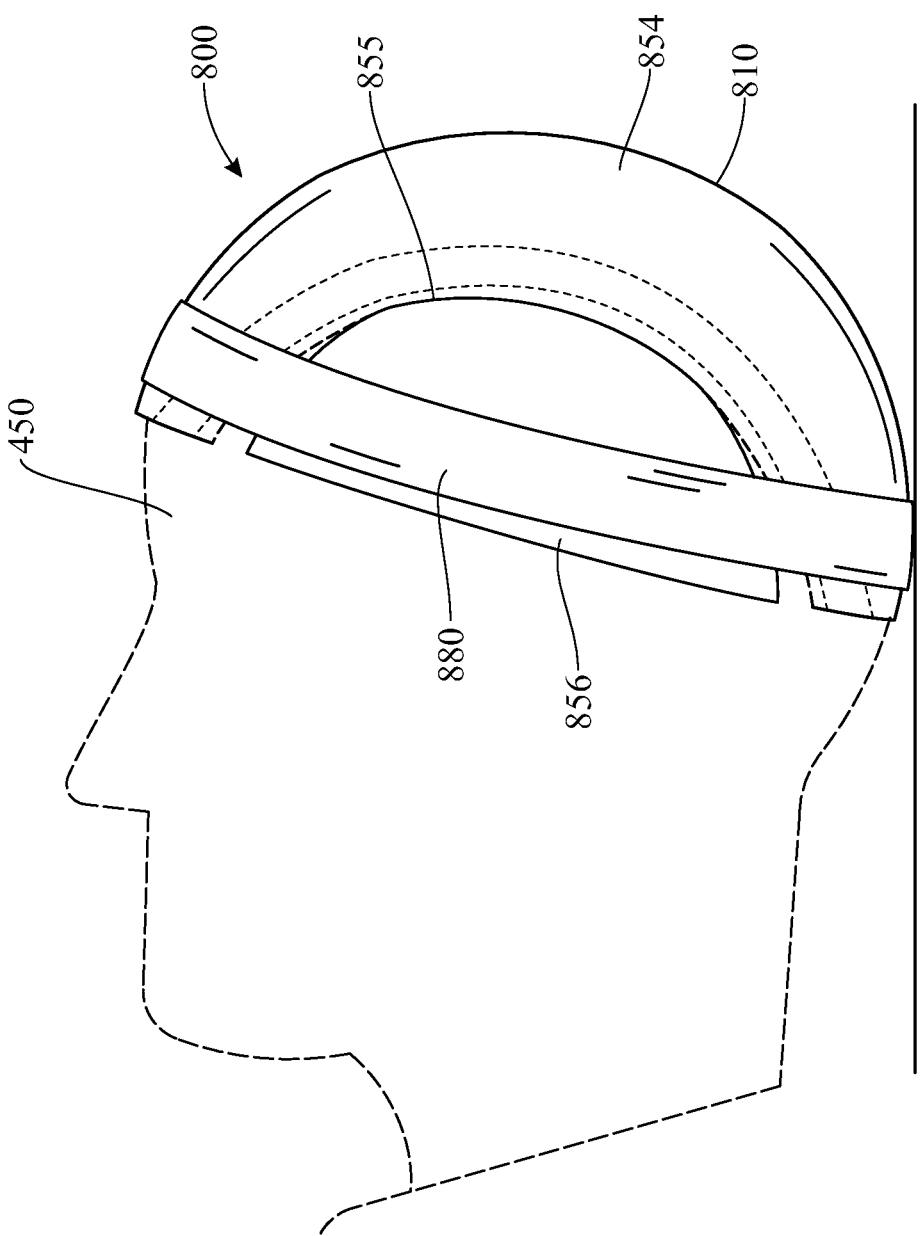
FIG. 17 presents a side view of the medical bandage of FIG. 16, with the pivotable side portions shown in a closed position, with straps securing the side portions in place and the medical bandage onto a person's head.

The illustrations of FIGS. 16 and 17 show a bandage 800 in accordance with a sixth exemplary embodiment of the invention. Like features of the bandage 800 of FIGS. 16 and 17 and the bandage 100 of FIGS. 1 through 7 are numbered the same except preceded by the numeral '8'. Similarly to previous embodiments, the medical bandage 800 comprises a main body 810 having an inner surface 820, an outer surface 824 and an inner cavity 822 delimited by the inner surface 820 for at least partially receiving a body part such as, but not limited to, a head 460. Similarly to previous embodiments, the main body 810 includes a skin-compatible first layer 840, a second layer 850, and a non-permeable third layer 860, the second layer 850 being sandwiched between the first and third layers 840 and 860 and comprising at least one space 852 through which the first and third layers 840 and 860 directly face one another. At least one through port 812 is arranged at said at least one space 852 (for instance, by perforating the first and third layers 840 and 860 in the area of the space 852, for example at or along a perforated or tearable seam 842), for accessing the inner cavity 822 of the main body 810 from outside the main body 810 and through the first, second and third layers 840, 850 and 860, or for stabilizing or supporting a drain or tubing passing through the port 812.

Similarly to the embodiment of FIGS. 1 through 3, the main body 810 of the present embodiment is comprised of several body portions. Specifically, the main body 810 is formed of a longitudinal body portion 854 and two opposite side body portions 856. As shown in FIG. 17, the longitudinal body portion 854 is configured to cover the head 450 or other protruding body part in a front-to-back arrangement, while the two opposite side body portions 856 are configured to be arranged on opposite sides of the longitudinal body portion 854 and cover sides of the head 450 or body portion, with the longitudinal and side body portions 854 and 856 forming a cap- or dome-shaped structure. In the present embodiment, however, at least one of the side body portions 856 is pivotably attached to the longitudinal body portion 854 along a hinge section 855, such that the pivotable side body portion 856 can pivotably switch between the aforementioned cap-shaped arrangement of FIG. 17 and an open position, shown in FIG. 16, in which the pivotable side body portion 856 is pivoted away from the cavity 822 and towards the longitudinal body portion 854.

This pivotable connection between the longitudinal body portion 854 and one or, preferably, both side body portions 856 facilitates donning the bandage 800 on the head 450 of a person in a supine position, as shown in FIGS. 16-17. Specifically, as shown in broken lines in FIG. 16, a medical professional may initially place the bandage 800 in the aforementioned open position (indicated with reference numeral 800'), and tuck a rear end 857 of the longitudinal body portion 854 underneath the person's head 450. Next, the medical professional may pull a front end 858 of the longitudinal body portion 854 towards the person's forehead, as indicated by arrow B, and place the longitudinal body portion 854 on or along the person's head 450 as shown. Once the longitudinal body portion 854 is deployed on the head 450, the side body portions 856 can be pivoted towards the head 450 as indicated by arrows C and placed on or near the sides of the head 450 as shown in FIG. 17. Finally, the straps 880 can be extended over the longitudinal and side body portions 854 and 856 to retain the side body portions 856 in the position of FIG. 17, i.e. to maintain the main body 810 in cap-shaped form and secure the main body 810 to the head 450.

Figure 18:
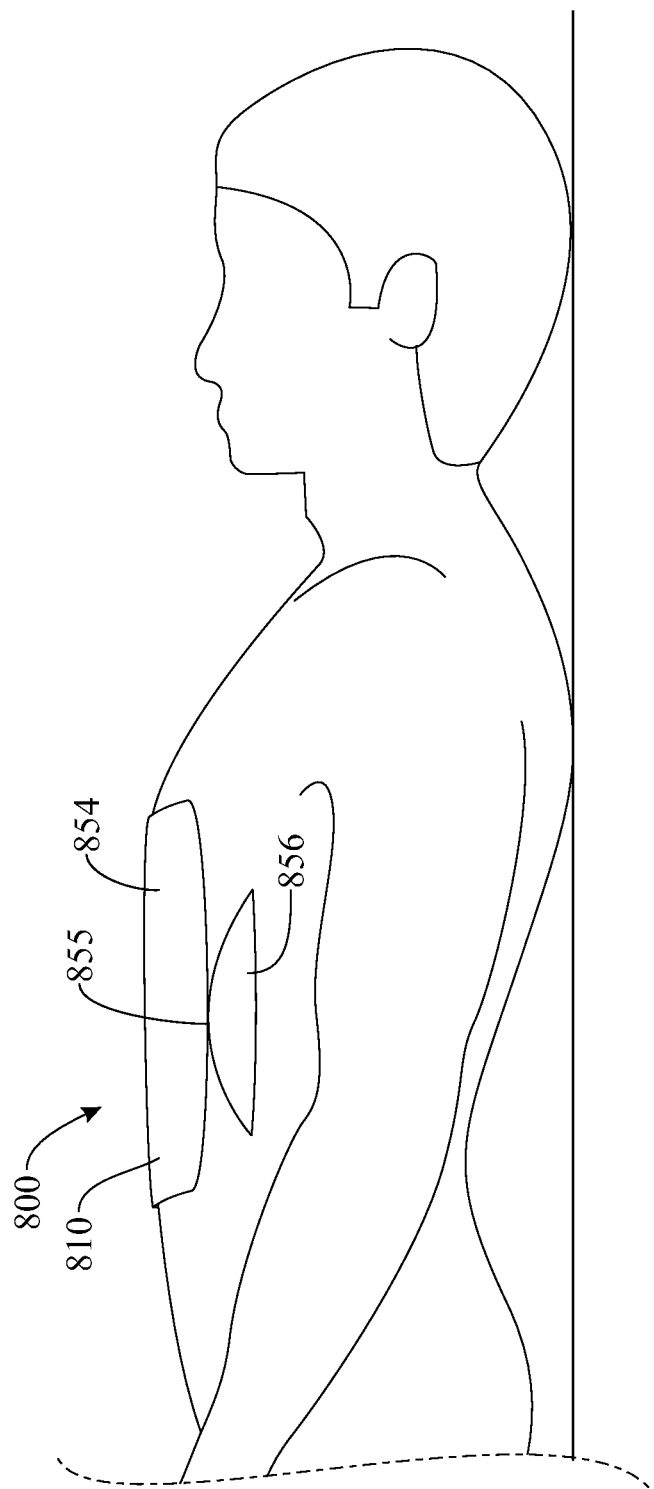
FIG. 18 presents a side view of the medical bandage of FIG. 16 shown in an extended position, covering a person's chest.

Because one or both of the side body portions 856 of the bandage 800 of FIG. 16 are pivotable relative to the longitudinal body portion 854, and both body portions 854, 856 are flexible or malleable (similarly to the rest of embodiments), the bandage 800 can adopt a myriad of positions and shapes by deforming the longitudinal body portion 854 and/or the side body portions 856, and pivoting the side body portions 856 relative to the longitudinal body portion 854. For instance and without limitation, as shown in FIG. 18, the longitudinal body portion 854 and side body portions 856 can adopt an extended position such that the main body 810 is relatively planar and can be used to cover a wider area of a person's body such as, but not limited to, the chest or thorax. For example, the bandage 800 can include an insulating material such as, but not limited to, biaxially-oriented polyethylene terephthalate (e.g., Mylar®), such as in the second layer 850, allowing the bandage to be used over the chest to prevent pneumothorax.

Figure 19:
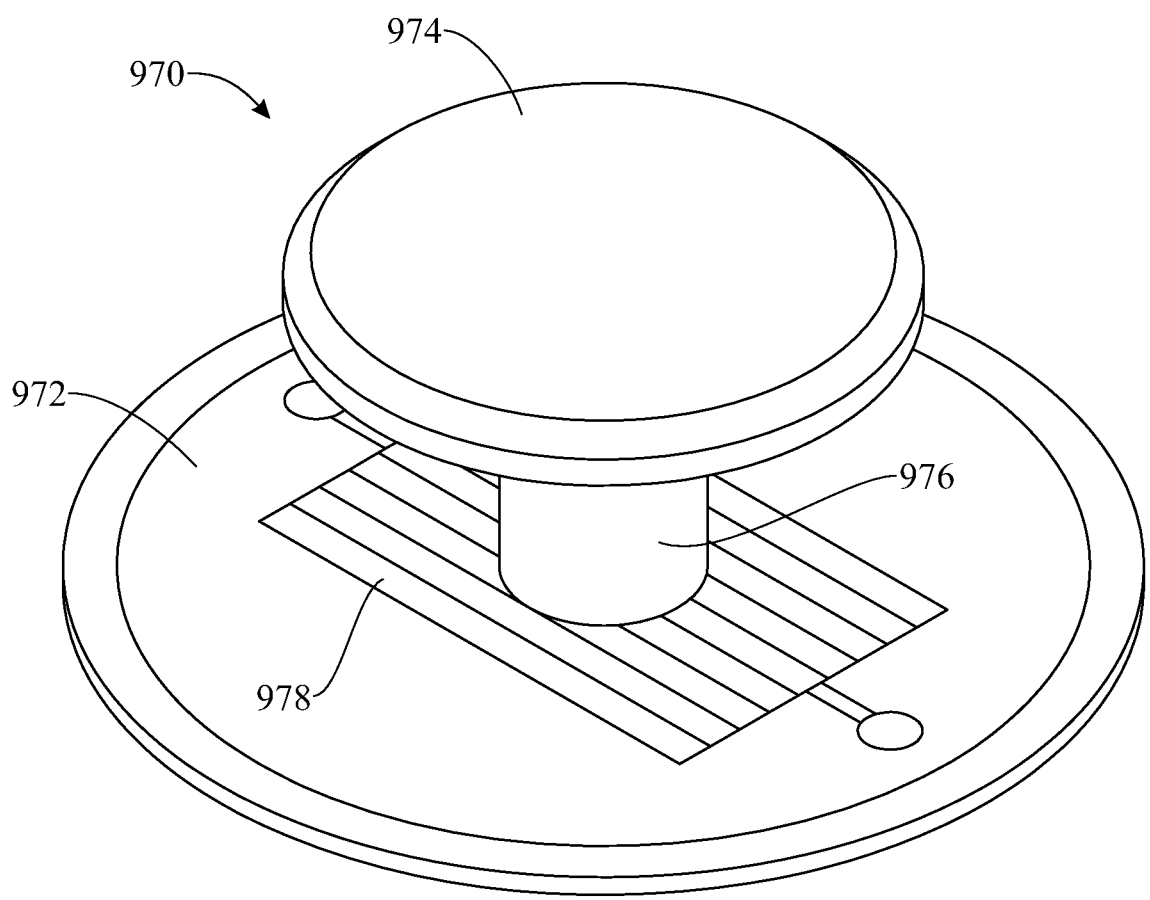
FIG. 19 presents a perspective view of a sensor comprised in a medical bandage in accordance with a seventh illustrative embodiment of the invention.
Figure 20:
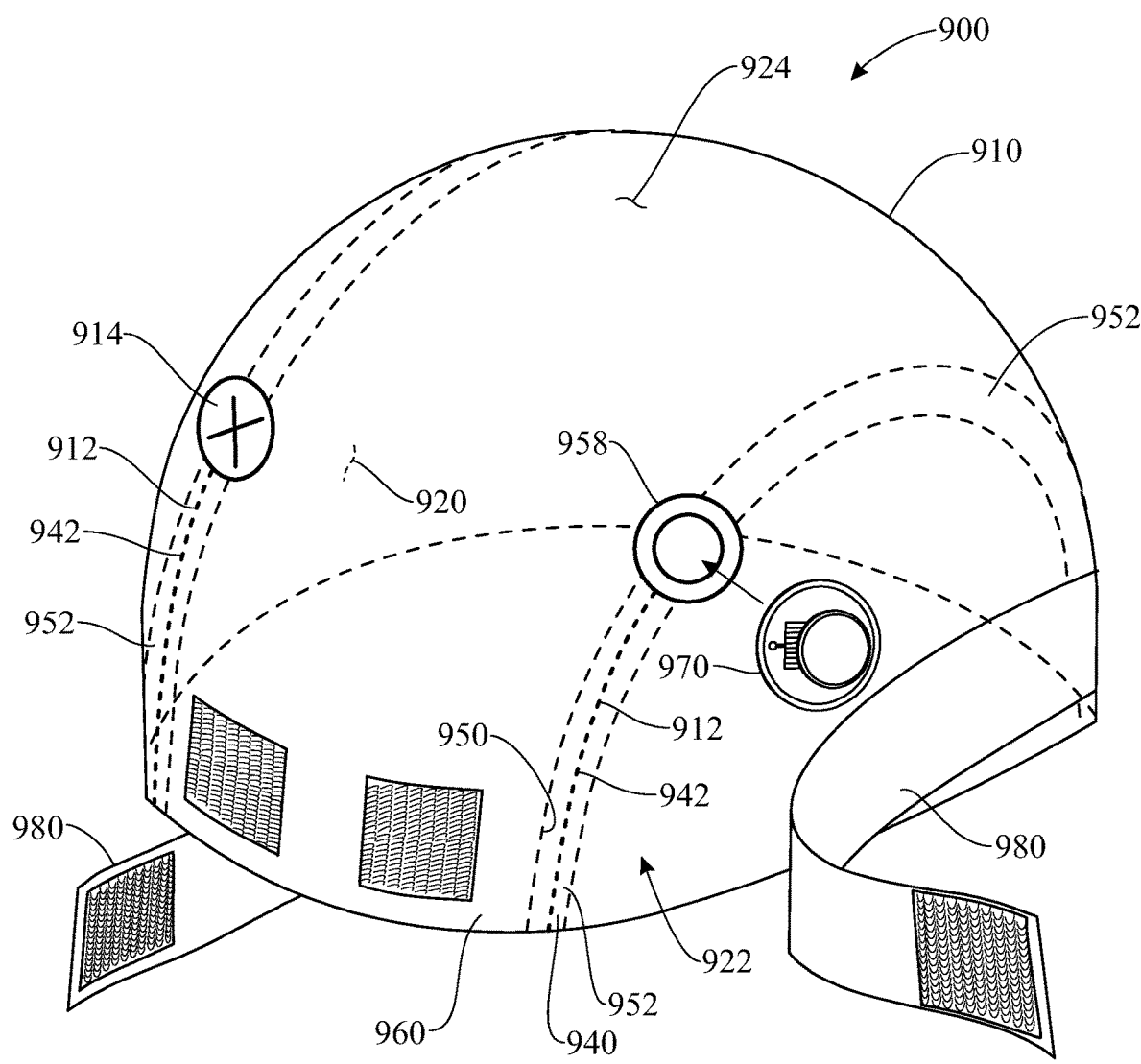
FIG. 20 presents the medical bandage in accordance with a seventh illustrative embodiment of the invention, showing the sensor being attached to a sensor connector comprised in the main body of the medical bandage.

The illustrations of FIGS. 19 through 22 show a bandage 900 in accordance with a seventh exemplary embodiment of the invention. Like features of the bandage 900 of FIGS. 19 through 22 and the bandage 100 of FIGS. 1 through 7 are numbered the same except preceded by the numeral '9'. As best shown in FIG. 20, similarly to previous embodiments, the medical bandage 900 comprises a main body 910 having an inner surface 920, an outer surface 924 and an inner cavity 922 delimited by the inner surface 920 for at least partially receiving a body part. Similarly to previous embodiments, the main body 910 includes a skin-compatible first layer 940, a second layer 950, and a non-permeable third layer 960, the second layer 950 being sandwiched between the first and third layers 940 and 960 and comprising at least one space 952 through which the first and third layers 940 and 960 directly face one another. At least one elongated through port 912 and/or discrete through port 914 is arranged at said at least one space 952, for accessing the inner cavity 922 of the main body 910 from outside the main body 910 and through the first, second and third layers 940, 950 and 960, or for stabilizing or supporting a drain or tubing passing through the port 912; for instance, the elongated through port 912 can be formed by perforating the first and third layers 940 and 960 in the area of the space 952, such as at or along a perforated or tearable seam 942.

With continued reference to FIG. 20, the bandage 900 of the present embodiment further comprises at least one sensor 970, such as a bioelectric sensor, configured to monitor one or more vital signs such as, but not limited to, pulse (heart rate), oxygen saturation, temperature, pressure (bandage pressure), blood pressure, moisture, bacterial concentration, presence of cerebrospinal fluid (CSF), ECG (electrocardiogram), electroencephalogram (EEG), thermal imaging, or sleep, or to monitor other physiological or cognitive status. The sensor 970 may be in wired or wireless (e.g., infrared or Bluetooth) communication with a monitoring device (e.g., smartphone 900 shown in FIG. 22). In some embodiments, the sensor 970 can include a color-coded light visible to the medical professional and indicative of the sensor measurements, for quick assessment of patient status.

Figure 21:
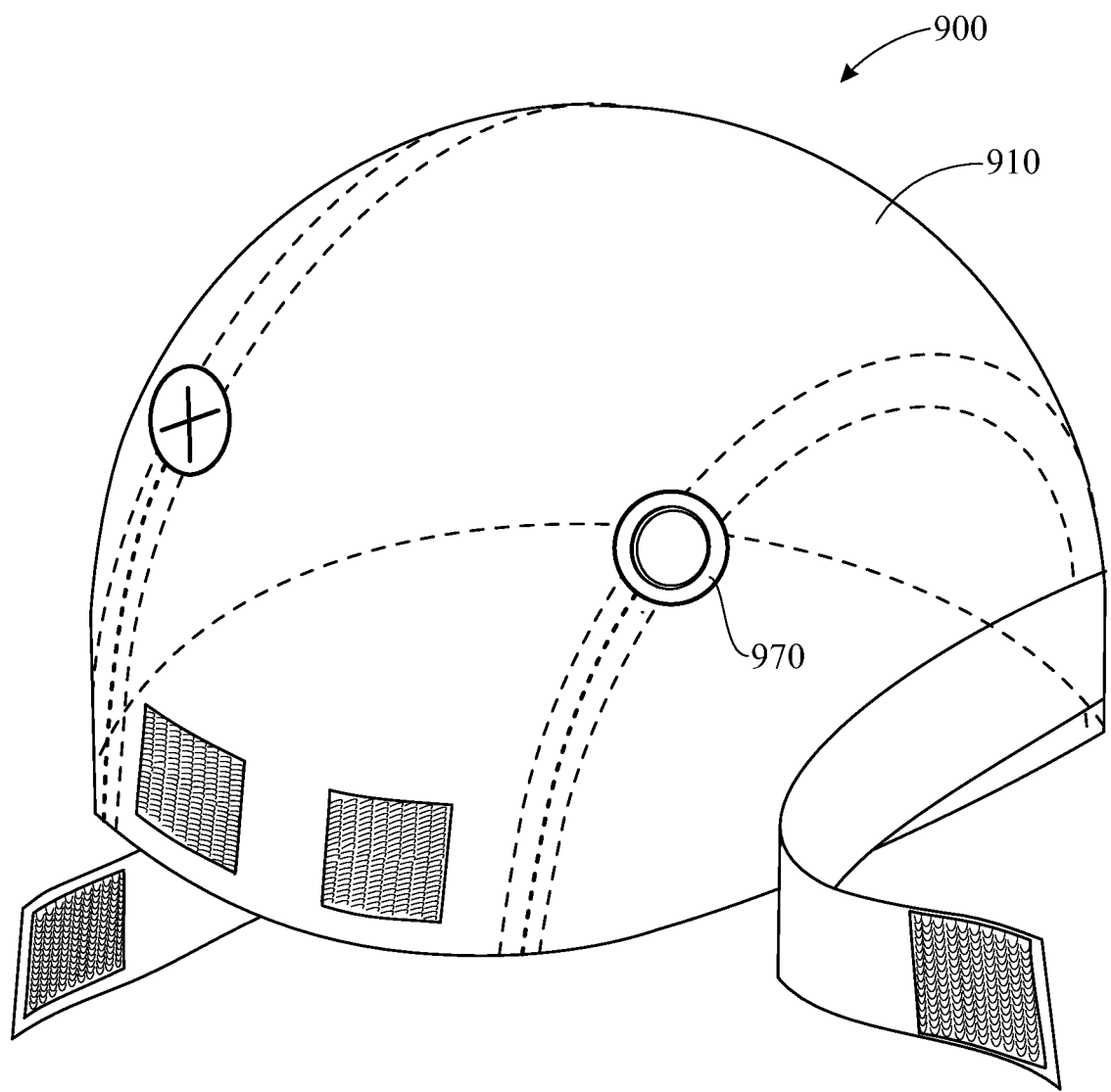
FIG. 21 presents the medical bandage of FIG. 20, with the sensor shown attached to the sensor connector.

In some embodiments, the sensor can be embedded in the bandage. In other embodiments, such as the present embodiment, the sensor 970 can be detachably connectable to the bandage 900, and more specifically, to the main body 910 of the bandage 900. For example, as shown in FIGS. 20 and 21, the sensor 970 can be selectively attached or detached from the sensor connector 958 in the main body 910.

The illustration of FIG. 19 shows an enlarged view of the sensor 970. As can be seen, the sensor 970 can include a bottom platform 972, a top platform 974 and a stem 976 extending between the bottom and top platforms 972 and 974. A sensor circuit 978 can be provided on at least one of the bottom platform 972, the top platform 974 and the stem 976 to be placed near a site of a pulse or site for wound and patient monitoring. For example, in the present embodiment, the sensor circuit 978 is arranged in the bottom platform 972, which is configured to be placed closer to the body part that will be covered by the bandage 900, allowing the sensor 970 to be placed directly over the site to be monitored (e.g., wound 462 shown in FIG. 22). The top and bottom platforms 972 and 974 may be round, as shown, or present alternative shapes such as square, rectangular, oval, etc.

In some embodiments, when a sensor 970 is not plugged into the sensor connector 958, the sensor connector 958 may also be used as a discrete port and serve the same purposes as the discrete through port 914 and other discrete through ports described herein with reference to the remaining embodiments. In other words, one or more discrete through ports provided in the bandage may be used as a sensor connector for detachably receiving a sensor.

Figure 22:
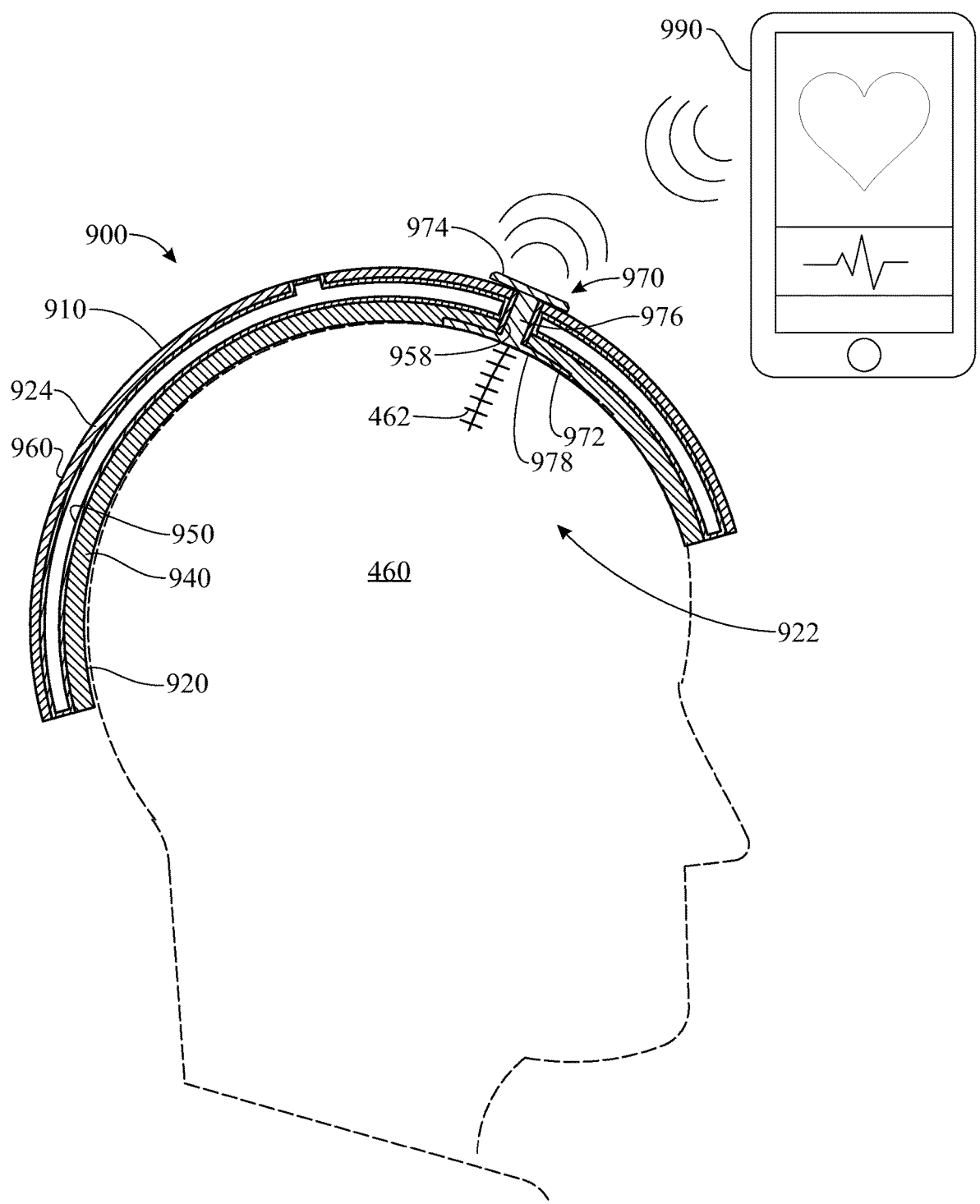
FIG. 22 presents a side view of the medical bandage of FIG. 20, with the sensor communicating wirelessly with an external electronic monitoring device.

In operation, as shown in FIG. 22, the bandage 900 is fitted onto the head 460 of a user to cover wound 462. The sensor connector 958 is oriented towards the wound 962 and the sensor 970 is inserted or plugged into the sensor connector 958 such that the sensor circuit 978 faces the wound 962. The sensor circuit 978 captures one or more measurements. A wired or wireless transmitter (not shown) comprised in the sensor transmits the measurement to a smartphone 990 or other monitoring device running a software application or program configured to process, store and/or visualize or present the measured data on a screen or other user interface, or carry out other operations with the measured data.

Alternative embodiments and uses of the invention are contemplated. For instance, the bandage can be used to cover alternative body parts to those shown in the drawings and/or described herein. Alternatively or additionally, the number and/or length of straps included in the bandage may vary.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims, including any amendments made during the pendency of this application, and all equivalents of those claims as issued.

What is claimed is:

1. A medical bandage comprising:
a deformable main body having an innermost surface and an outermost surface, wherein the main body is configured to adopt a cap-shaped configuration in which an inner cavity delimited by the innermost surface for at least partially receiving a head, limb, stump, finger or other body part, and further in which the outermost surface is arranged on an outer side of the main body, wherein at least part of said main body comprises:
a skin-compatible first layer,
a second layer,
a non-permeable third layer, wherein
the first layer is arranged closer to the inner cavity than the third layer, and further wherein
the second layer is arranged between the first layer and the third layer and comprises at least one space through which the first and third layers directly face one another, and
at least one through port arranged at said at least one space, for accessing the inner cavity of the main body from the outer side of the main body and through the first, second and third layers, or for stabilizing or supporting a drain or tubing passing through the through port; and
one or more sensors configured to monitor one or more body conditions; wherein
the medical bandage is configured to adopt a usage configuration in which the main body is arranged in the cap-shaped configuration and the one or more sensors extend from the outermost surface of the main body to the innermost surface of the main body through the first layer, through the at least one space, and through the third layer, and further in which a respective first end of each of the one or more sensors is arranged facing the inner cavity and a respective opposite, second end of each of the one or more sensors is arranged on the outer side of the main body; and further wherein
at least one sensor of the one or more sensors comprises a light emitter configured to emit a color-coded light visible from outside the medical bandage and indicative of measurements by said one or more sensors.

2. The medical bandage of claim 1, wherein said at least one through port is provided by scored lines and can adopt a closed position in which the scored lines are not torn, and an open position in which the scored lines are torn open providing quick access to the inner cavity.

3. The medical bandage of claim 1, wherein the second layer comprises an absorbent material, and the first layer is permeable to the passing of fluid from the innermost surface towards the second layer.

4. The medical bandage of claim 1, wherein the main body further comprises at least one adjustment strap, configured to adjustably attach two different sections of the main body.

5. The medical bandage of claim 4, wherein the adjustment strap is fixedly attached to a first section of the main body and disconnectably attachable to a second section of the main body.

6. The medical bandage of claim 4, wherein opposite ends of the adjustment strap are disconnectably attachable to different sections of the main body.

7. The medical bandage of claim 4, wherein said main body in the cap-shaped configuration comprises a rim defining an opening for inserting a head, limb, stump, finger or other body part therethrough towards the inner cavity of the main body, wherein said at least one adjustment strap is attachable along said rim and parallel to said rim.

8. The medical bandage of claim 4, wherein the at least one adjustment strap comprises two adjustment straps configured to wind with one another and attach to the main body by a respective hook-and-loop connection.

9. The medical bandage of claim 4, wherein the at least one adjustment strap comprises two adjustment straps configured to tie to one another into a knot for compression or securing the bandage.

10. The medical bandage of claim 1, wherein at least one of the first, second and third layers comprises an insulating material.

11. The medical bandage of claim 1, wherein the main body is at least partially elastic to adjustably fit onto a head, limb, stump, finger or other body part.

12. The medical bandage of claim 1, wherein the first, second and/or third layers comprise a plurality of partial portions, which are arranged adjacently to each other forming a cap-shape.

13. The medical bandage of claim 12, wherein at least two partial portions of the second layer are separated by a gap, through which the first and third layers directly face one another.

14. The medical bandage of claim 13, wherein the first layer and layer comprise at least one pair of perforated seams facing the gap.

15. The medical bandage of claim 12, wherein the plurality of partial portions comprises an elongated body portion and two opposite side portions attached to opposite sides of the elongated body portion, wherein one or both of the opposite side portions are pivotable relative to the elongated body portion and configured to adopt a closed position in which the side portions and elongated body portion form a cap-shaped body.

16. The medical bandage of claim 1, wherein the main body comprises a tearable portion which is configured to be torn off and removed from a remainder of the main body to reduce the height of the main body, wherein the tearable portion, once torn off and removed from said remainder of the main body, is usable as a tourniquet.

17. The medical bandage of claim 1, wherein at least one sensor of the one or more sensors is configured to establish wired or wireless communication with an external electronic device for transmitting a measurement to said electronic device.

18. The medical bandage of claim 1, wherein at least one sensor of the one or more sensors is disconnectably attachable to the at least one through port.

19. The medical bandage of claim 1, further comprising a coagulant agent carried by the main body, wherein, in the usage configuration of the medical bandage, the coagulant agent is arranged on the innermost surface of the main body.

20. The medical bandage of claim 1, wherein the one or more sensors comprise a sensor selected from the group consisting of a pulse sensor, an oxygen saturation sensor, a temperature sensor, a bandage pressure sensor, a blood pressure sensor, a moisture sensor, a bacterial concentration sensor, a cerebrospinal fluid (CSF) sensor, an electrocardiogram (ECG) sensor, an electroencephalogram (EEG) sensor, a thermal imaging sensor, and a sleep sensor.

21. The medical bandage of claim 1, wherein at least one sensor of the one or more sensors is disconnectably attached to the main body of the medical bandage.

22. The medical bandage of claim 1, wherein at least one sensor of the one or more sensors is attached to a sensor connector, the sensor connector comprised in the main body of the medical bandage.

23. The medical bandage of claim 22, wherein said at least one sensor of the one or more sensors is disconnectably attached to said sensor connector.

24. The medical bandage of claim 22, wherein the sensor connector is provided by a port of the at least one through port.

25. The medical bandage of claim 1, wherein at least one sensor of the one or more sensors comprises a bottom platform, a top platform, a stem extending between the bottom and top platforms, and a sensor circuit provided in at least one of the bottom platform, the top platform.

26. The medical bandage of claim 1, wherein at least one sensor of the one or more sensors comprises a bottom platform, a top platform, a stem extending between the bottom and top platforms, and a sensor circuit provided in the bottom platform.

27. The medical bandage of claim 1, wherein at least one sensor of the one or more sensors is arranged in a location on the main body configured to be placed at or near a pulse site of the subject.

28. A medical bandage comprising:
a deformable main body having an innermost surface and an outermost surface, wherein the main body is configured to adopt a cap-shaped configuration in which an inner cavity is delimited by the innermost surface for at least partially receiving a head, limb, stump, finger or other body part, and further in which the outermost surface is arranged on an outer side of the main body, wherein at least part of said main body comprises:
a skin-compatible first layer,
a second layer,
a non-permeable third layer, wherein
the first layer is arranged closer to the inner cavity than the third layer, and further wherein
the second layer is arranged between the first layer and the third layer and comprises at least one space through which the first and third layers directly face one another, and
at least one through port arranged at said at least one space, for accessing the inner cavity of the main body from the outer side of the main body and through the first, second and third layers, or for stabilizing or supporting a drain or tubing passing through the through port; and
one or more sensors configured to monitor one or more body conditions; wherein
the medical bandage is configured to adopt a usage configuration in which the main body is arranged in the cap-shaped configuration and each sensor of the one or more sensors extends from the outermost surface of the main body to the innermost surface of the main body through the first layer, through a respective port of the at least one port, and through the third layer, and further in which a respective first end of said each sensor is arranged facing the inner cavity and a respective opposite, second end of said each sensor is arranged on the outer side of the main body; and further wherein
at least one sensor of the one or more sensors comprises a light emitter configured to emit a color-coded light visible from outside the medical bandage and indicative of measurements by said one or more sensors.

29. A medical bandage comprising:
a deformable main body having an innermost surface and an outermost surface, wherein the main body is configured to adopt a cap-shaped configuration in which an inner cavity is delimited by the innermost surface for at least partially receiving a subject's head, limb, stump, finger or other body part, and further in which the outermost surface is arranged on an outer side of the main body; and one or more sensors configured to monitor one or more body conditions; wherein the medical bandage is configured to adopt a usage configuration in which the main body is arranged in the cap-shaped configuration and the one or more sensors extend through the main body, from the outermost surface of the main body to the innermost surface of the main body, and further in which a respective first end of each of the one or more sensors is arranged facing the inner cavity and a respective opposite, second end of each of the one or more sensors is arranged on the outer side of the main body; and further wherein at least one sensor of the one or more sensors comprises a light emitter configured to emit a color-coded light visible from outside the medical bandage and indicative of measurements by said one or more sensors.

\* \* \* \* \*